United States Patent [19]

Fanselow et al.

[11] Patent Number: 5,562,127

[45] Date of Patent: Oct. 8, 1996

[54] FLEXIBLE, CHLORINE FREE MULTILAYERED TUBING

[75] Inventors: Dan L. Fanselow, White Bear Lake; Walton J. Hammar, St. Paul; John H. Ko, Woodbury; James C. Margl, Oakdale; Debra L. Wilfong, Lake Elmo, all of Minn.

[73] Assignee: Minnesota Mining and Manufacturing Company, St. Paul, Minn.

[21] Appl. No.: 503,537

[22] Filed: Jul. 18, 1995

Related U.S. Application Data

[63] Continuation-in-part of Ser. No. 104,256, Aug. 10, 1993, abandoned, which is a continuation-in-part of Ser. No. 103,328, Aug. 6, 1993, abandoned.

[51] Int. Cl.$^6$ .................................................... F16L 11/04
[52] U.S. Cl. .......................... 138/137; 138/141; 138/178; 604/264
[58] Field of Search ..................................... 138/137, 141, 138/140, 174, 177, 178; 428/36.6, 36.9, 36.91; 604/264, 280

[56] References Cited

U.S. PATENT DOCUMENTS

| | | | |
|---|---|---|---|
| 3,287,315 | 11/1966 | Connor et al. | 138/137 |
| 3,384,089 | 5/1968 | Shriner | 138/137 |
| 3,429,954 | 2/1969 | Atkins et al. | 138/137 |
| 3,561,493 | 2/1971 | Maillard | 138/141 |
| 3,584,656 | 6/1971 | Van Assendelet | 138/137 |
| 4,044,799 | 8/1977 | Higbee et al. | 138/137 |
| 4,190,088 | 2/1980 | Lalikos et al. | 138/137 |
| 4,211,741 | 7/1980 | Ostoich | 138/137 |
| 4,272,559 | 6/1981 | Asai et al. | 427/54.1 |
| 4,298,714 | 11/1981 | Levin et al. | 525/330 |
| 4,305,983 | 12/1981 | Hoppe et al. | 428/36 |
| 4,627,844 | 12/1986 | Schmitt | 138/137 |
| 4,643,926 | 2/1987 | Mueller | 138/137 |
| 4,685,090 | 8/1987 | Krevor | 138/137 |
| 4,707,389 | 11/1987 | Ward | 428/36 |
| 4,948,643 | 8/1990 | Mueller | 138/137 |
| 5,059,375 | 10/1991 | Lindsay | 264/167 |
| 5,085,649 | 2/1992 | Flynn | 604/282 |
| 5,158,836 | 10/1992 | Schirmer et al. | 428/336 |
| 5,198,301 | 3/1993 | Hager et al. | 428/355 |

FOREIGN PATENT DOCUMENTS

| | | |
|---|---|---|
| 0380270 | 8/1990 | European Pat. Off. . |
| 0422632 | 4/1991 | European Pat. Off. . |
| 0448886 | 10/1991 | European Pat. Off. . |
| 0477025A2 | 3/1992 | European Pat. Off. ........ B32B 27/08 |
| WO93/23093 | 11/1993 | WIPO . |
| WO94/08769 | 4/1994 | WIPO . |

OTHER PUBLICATIONS

PCT Search Report for PCT/US94/07729, filed 07 Dec. 1994.

Paprock, J., The MHA Recycling & Conservation Guide, Minnesota Hospital Association, 1991.

Ellis, J. R., "Plasticizers—Under Scrutiny Again," Medical Device & Diagnostic Industry, vol. 13, No. 3, pp. 88–89, Mar. 1991.

Menagh, M., "The Business of Going Green," OMNI, vol. 13, No. 9, pp. 42–48, Jun. 1991.

Erickson, D., "Can plastics be burned safely?," Plastics World, Sep. 1989.

Encyclopedia of Polymer Science and Engineering, vol. 17, pp. 50–51, John Wiley & Sons, 1989.

(List continued on next page.)

Primary Examiner—James E. Bryant, III
Attorney, Agent, or Firm—Gary L. Griswold; Walter N. Kirn; F. Andrew Ubel

[57] ABSTRACT

Multilayered tubing which exhibits one or more desirable characteristics of polyvinyl chloride (PVC) tubings, such as clarity, flexibility and toughness, but without the environmental and health hazards associated with PVC materials, is provided. Also provided is a method of preparing such tubing.

31 Claims, 4 Drawing Sheets

OTHER PUBLICATIONS

"Proposed Dioxins Control Measure for Medical Waste Incinerators," Staff Report—State of California Air Resources Board Stationary Source Division, May 25, 1990.

Taravella, S., "Hospitals Dispose of Destructive Waste Habits," Modern Healthcare, pp. 26–30, Dec. 24/31, 1990.

Vogg, H., et al., "Contribution to Solving the Problem of Dioxins Generated during Waste Incineration," Chem. Eng. Technol. 13 (1990) pp. 221–229.

"Dioxin and Other Pollutants from Incineration of Medical Waste," Perspectives on Medical Waste, A Report of The Nelson A. Rockefeller Institute of Government, State University of New York, Sponsored by the Medical Waste Policy Committee, Jun. 1989, pp. II.20–II–24.

PCT Search Report for PCT/US94/07729.

FLEXIBLE, CHLORINE FREE MULTILAYERED TUBING

This is a continuation of application Ser. No. 08/104,256, filed Aug. 10, 1993, abandoned which is a continuation-in-part of application Ser. No. 08/103,328, filed Aug. 6, 1993, now abandoned.

FIELD OF THE INVENTION

This invention relates to multilayered structures, such as tubing, which are suitable to replace conventional polyvinyl chloride (PVC) tubing, but without the environmental and health hazards associated with PVC materials.

BACKGROUND OF THE INVENTION

Polyvinyl chloride (PVC) based tubing is used in numerous medical products. However, PVC is viewed as hazardous to both the environment and to personal health. Incineration of PVC results in the release of hydrochloric acid (HCl), and PVC is viewed as a major contributor to HCl in incinerator flue gases. Also, PVC is suspected of contributing to polychlorinated dibenzodioxin and furan toxins formed during incineration. Levels of these toxins are up to three times greater in medical infectious waste as compared to municipal waste streams. In addition to incineration concerns, exposure to di-2-ethylhexyl phthalate (DEHP), a common plasticizer used with PVC, may present a number of health related concerns, including reduced blood platelet efficacy and potential links to liver cancer.

Despite these concerns, PVC-based tubing and articles constructed therefrom, continue to be the material of choice in scientific and medical applications. See, e.g., *Encyclopedia of Polymer-Science and Technology*, Vol. 17, pg. 50 (1989). The continued use of PVC materials is due, at least in part, to PVC's attractive qualities, including flexibility; toughness; resistance to UV light, solvents, cuts, scratches, and acids; clarity or opaqueness as required; and low cost. In addition, PVC's properties can be modified through the addition of various additives, such as plasticizers, colorants, and the like. For example, U.S. Pat. No. 4,298,714 discloses a modified PVC material with reduced hydrophilicity due to the addition of various thiol-group compounds to the PVC backbone.

Other thermoplastic polymers have been used to form single-layer tubing. For example, low-density polyethylene, high density polyethylene, polypropylene, ethylene vinyl acetate, and polybutylene have all been used to form single-layer tubings. See, e.g., *Encyclopedia of Polymer Science and Technology*, Vol. 17, pp. 50–51 (1989). However, none of these polymer materials has been successfully used to provide tubing with the advantageous properties needed to serve as an environmentally compatible replacement for PVC-based materials.

Multilayered tubing which utilizes different polymers in the respective layers has also been developed. Specifically, such a multilayered tubing allows the bonding together of previously incompatible materials, such as PVC and ethylene vinyl acetate copolymer (EVA). For example, U.S. Pat. No. 4,707,389 discloses a multilayered tube composed of an outer layer of EVA and an inner layer of PVC, bonded together by a bonding layer. In addition to continued environmental incompatibility, this tubing tends to delaminate during continuous usage. To avoid delamination problems, U.S. Pat. No. 3,561,493 provided a multilayered tubing in which the inner and outer layers are welded together by a precompounded layer of the two different polymers. However, chlorine-containing polymers, such as PVC, are still considered for use in such tubings.

To date, no multilayered tubing exists which provides the advantageous characteristics of PVC materials, and yet is free of leachable contaminants and is environmentally compatible.

Therefore, there is a need for an environmentally compatible multilayered tubing that can be utilized in a wide range of both medical and nonmedical products, and that can serve as a replacement for PVC-based materials. Specifically, there is a need for PVC replacement tubing that would be both flexible, kink-resistant, and tough (i.e., scratch- and cut-resistant), as well as solvent and UV light resistant, clear or opaque as need be, and could be made for a relatively low cost.

SUMMARY OF THE INVENTION

The present invention is directed to multilayered tubing having a bore, a wall composed of multiple layers of thermoplastic polymer, and outside and inside wall surfaces. The wall layers include at least an inner layer and an outside surface layer. The inner layer acts as the flexible core of the wall and in preferred embodiments constitutes the major portion of the wall thickness. Additional layers such as an inside surface layer and internal layers other than the inner layer may also be present. When the tubing wall is composed of a minimum of two layers, the inner layer forms the inside surface of the wall as well as being the flexible core of the wall.

The inner layer is composed of at least one chlorine-free, first thermoplastic polymer or a mixture of such thermoplastic polymers or a mixture with other substances and polymers. The outside surface layer is composed of at least one chlorine-free, second thermoplastic polymer or a mixture of such thermoplastic polymers or a mixture with other substances and polymers. The optional inside surface layer is composed of at least one chlorine-free third thermoplastic polymer or a mixture of such thermoplastic polymers or a mixture with other substances or polymers. The additional internal layers may be composed of at least of one of the first, second or third thermoplastic polymers or a mixture of such thermoplastic polymers alone or with other substances and polymers.

The first thermoplastic polymer has a flexibility that mimics or is greater than that of polyvinyl chloride used to make medical tubing. In particular, it has a flexibility that substantially achieves tubing functions ranging from a capability to flex and be pushed through a curved lumen of a body part, to a capability to be formed into an acute curve without creating a cross-sectional crease which would stop the flow of fluid or air passing through the tubing bore. More specifically, the first thermoplastic polymer has a flexibility that is measured as a Young's modulus that substantially mimics or is less than that of polyvinyl chloride used for medical tubing. Preferably, the first thermoplastic polymer Young's modulus ranges from about 2 to about 60 MPa (megaPascals), more preferably from about 10 to about 40 MPa especially preferably from about 15 to about 30 MPa.

The second thermoplastic polymer is tough and has an abrasion resistance that substantially mimics that of polyvinyl chloride used for medical tubing. It has a Young's modulus up to about fifteen times the Young's modulus of the first thermoplastic polymer. Preferably this ratio is up to a maximum of about seven times, more preferably, in a range of from about equal to, up to about three times, the Young's modulus of the first thermoplastic polymer. Especially preferably, this ratio is greater than, up to about three times, the Young's modulus of the first thermoplastic polymer. Preferably, the Young's modulus of the second thermoplastic polymer ranges from about 15 to about 300 MPa, more preferably from about 20 to 150 MPa, more especially preferably from about 20 to 45 MPa.

The third thermoplastic polymer has the same characteristics as the second thermoplastic polymer. The chemical identities of these two polymers can differ.

Any thermoplastic polymer having the characteristics described above is appropriate for use as a first, second or third thermoplastic polymer. Generally, the first, second and third thermoplastic polymers have backbones of any configuration and chemical structure that will maintain the foregoing characteristics and thermoplasticity during multi-layered tube formation. Backbone configurations include but are not limited to linear, cross-linked, branched, random, grafted, block, crystalline-amorphous domain, pseudo-cross-linked and ionomeric. Backbone chemical structures include polyolefin, polyester, polyurethane, polyvinyl alcohol, polyacrylates, polymethacrylates and polyvinyl substituents such as vinyl acetate. Preferred thermoplastic polymers include the polymers of olefin monomers as well as copolymers of olefin monomers and substituted olefin monomers. Especially preferred olefin monomers include C2 to C4 mono-unsaturated alkenes and especially preferred substituted olefin monomers include C4 to C14 mono-unsaturated alkenes, C8 to C14 aryl alkenes, and C2 to C6 mono-unsaturated alkenes having moieties selected from the group consisting of oxyalkanoyl, carboxy, carboxamide and alkoxycarbonyl of 1 to 6 carbons. The use of such a thermoplastic polymer as a first, second or third thermoplastic polymer depends, but is not limited to, the percent of substituted olefin monomer present in the polymer, the degree of regular molecular orientation achieved by the polymer, the percent of crystallinity, the degree of cross-linking, pseudo-cross-linking or ionomericity present, the degree of backbone three dimensional rotation allowed by the chemical backbone structure, and the nature of the monomer constituting the majority of the polymerized unit in the polymer.

By combining the respective flexibility and abrasion resistant characteristics of at least the first and second thermoplastic polymers, the multilayered tubing of the invention has a wall outside surface that exhibits a tough, protective character and a wall core that exhibits conformable, resilient, flexive properties. In cooperation, the wall layers provide a multilayer tubing that is approximately as flexible, as resilient and as kink/rekink resistant as, and in preferred embodiments exceed those characteristics of, PVC medical tubing. The wall layers also provide a multilayer tubing as durable and as scratch/abrasion resistant as PVC medical tubing.

The multilayer tubing can have several configurations including two layer, three layer and a multi (more than three) layer configurations. In the two layer configuration, the outside surface layer overlays the inner layer. The inner layer of this configuration forms the inside surface of the tubing wall and also acts as the core of the wall. In the three layer configuration, the second and third thermoplastic polymers form the outside and inside surface layers respectively and the first thermoplastic polymer forms the inner layer which acts as the core of the wall. Other configurations such as a five layer configuration are also within the invention. In these configurations, the first thermoplastic polymer forms an inner layer or layers which act as the core of the tubing wall while the second and third thermoplastic polymers form the inside and outside surface layers.

The multilayered tubing of the present invention preferably does not release harmful chemicals such as hydrogen chloride to the atmosphere when it is burned or otherwise degraded. The multilayered tubing is also safe and effective for use in medical applications. It preferably contains no plasticizer or other leachable or exudable ingredient in at least the layer forming the inside surface of the wall which could contaminate fluids. In particular, at least the first and third thermoplastic polymers contain no phthalate or citrate esters or other plasticizers and no or substantially little additive which are capable of leaching into fluids. The multilayered tubing also preferably has an ability to avoid absorption of solvents, drugs, pharmaceutical agents and other materials which come in contact with the tubing. This property is especially desirable when the tubing is used as medical tubing. In this application, the layer forming the inside surface of the tubing wall displays minimal or no absorption of drug, pharmaceutical carrier or other pharmaceutical liquid. Optionally, the tubing layers can be composed of thermoplastic polymers which will make the layers resistant to acid, solvent, UV light, and will render the tubing clear or opaque or colored.

The present invention is as well directed to a method for making the multilayered tubing. According to this method, at least one flexible, chlorine-free first thermoplastic polymer and at least one tough, chlorine-free second thermoplastic polymer are coextruded as at least the inner and outside surface layers of the tubing wall. Additional thermoplastic polymers such as the third thermoplastic polymer can be coextruded to form additional layers of the tubing wall. The coextrusion conditions of pressure and heat cause the thermoplastic polymers to become melts so that they coextrude as seamless united layers of the tubing wall. Preferably, the multilayered tubing is passed through a cooling fluid after its formation at the coextrusion die. Air or another gas can be passed through the bore of the multilayered tubing during its formation and cooling so that the wall does not collapse.

DETAILED DESCRIPTION OF THE INVENTION

Figure 1:
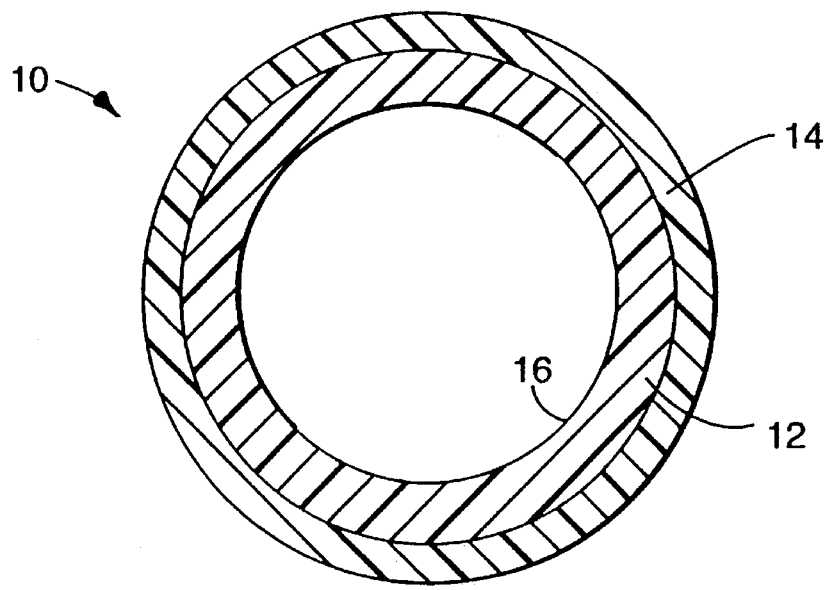
FIG. 1 is a cross-sectional illustration of a first embodiment of a multilayered tubing of two layered wall construction.

The multilayered tubing of the present invention possesses physical characteristics much like those of polyvinyl chloride medical tubing. In addition, the multilayered tubing is environmentally safe and avoids medical, pharmaceutical and health-related drawbacks of polyvinyl chloride tubing as mentioned above.

The wall of the multilayered tubing is made of multiple layers of thermoplastic polymer. The multiple layers provide composite characteristics so that the wall mimics and in preferred embodiments is better than PVC for many uses. A minimum number of layers for the wall is two: an outer surface layer and an inner layer. A majority of the wall thickness is preferably provided by the inner layer. This layer acts as the core of the wall to provide such characteristics as flexibility, and resilience to the multilayered tubing. Other layers such as the outside surface layer and, in a wall configuration of three or more layers, the inside surface layer, provide toughness, tensile strength and abrasion-resistance to the tubing. These layers are generally thinner than the layer or layers making up the flexible core of the wall so that their physical characteristics do not dominate the composite characteristics of the multilayered tubing.

Physical Characteristics

Toughness and resistance toward abrasion and cuts as well as high flexibility are physical characteristics that are important for medical tubing. The medical tubing preferably can survive the long term abrasion forces of such medical instruments as infusion pumps and friction fittings. It also preferably has a high flexibility so that it can be formed into tight loops and bends which are important for catheter formation and delivery tube service.

Tough, abrasion resistant thermoplastic polymers typically are not flexible enough for use in such medical tubing. Highly flexible thermoplastic polymers typically are not tough enough for use in such medical tubing. Consequently, until the present invention, a multilayer tubing had not been developed which exhibited toughness, significant tensile strength and abrasion resistance yet was flexible and kink/rekink resistant. In particular, a multilayered tubing mimicking PVC medical tubing had not been developed.

According to the present invention, a multilayered tubing has been developed which has a flexibility, a kink/rekink resistance, a tensile strength, a toughness and an abrasion resistance mimicking or exceeding PVC. The multilayered tubing has a wall composed of a core of at least one inner layer of at least one flexible chlorine-free first thermoplastic polymer and an outside surface layer of at least one tough, chlorine-free second thermoplastic polymer. When the wall contains three or more layers, there is also an inside surface layer of at least one tough, chlorine-free third thermoplastic polymer. One or more optional layers of at least the first, second or third thermoplastic polymer can also be included in the wall. Although it is preferred to use one thermoplastic polymer for a wall layer, such layers may also be composed of physical mixtures of thermoplastic polymers. To achieve the foregoing characteristics, the multilayered tubing incorporates at least the following parameters a through c and preferably the remaining parameters as well.

a. The first thermoplastic polymer has a flexibility mimicing or greater than that of polyvinyl chloride medical tubing. More specifically, the first thermoplastic polymer has a flexibility substantially needed to achieve a flex function for the tubing which ranges from a capability to flex through body part lumen to a capability to be formed into an acute curve without creating a cross-sectional crease which would stop the flow of fluid or air passing through the tubing bore. Preferably the flexibility of the first thermoplastic polymer is measured by its Young's modulus which in especially preferred embodiments is within a range of about 2 to about 60 MPa (megaPascals).

Examples of PVC medical tubing acting as reference points for the flexibility mimicked by the first thermoplastic polymer include but are not limited to arthroscopic tubes, coronary artery bypass tubes, infusion pump tubes, catheters, dialysis tubes, peritoneal lavage tubes, respiratory tubes, endotracheal tubes, gastric feeding tubes, wound drainage tubes, urinary catheter tubes, IV sets, angioplasty tubes and general purpose PVC tubing such as "Tygon™" brand PVC tubing manufactured by Norton Performance Plastics, Wayne, N.J. These tubes range in flexibility from a stiff endotracheal tube to a flexible arthroscopic tube to a highly flexible IV set. The Young's modulus of the PVC's used in such tubes ranges from about 2 MPa to about 100 MPa.

b. The second thermoplastic polymer has a Young's modulus that is not more than about fifteen times, preferably from about equal to, up to no greater than, about fifteen times, more preferably within a range of greater than, up to about fifteen times, the Young's modulus of the first thermoplastic polymer. Especially preferably, the Young's modulus of the second thermoplastic polymer is up to no more than about seven times, most preferably up to no more than about three times, the Young's modulus of the first thermoplastic polymer. Preferred embodiments have a Young's modulus of the second thermoplastic polymer within a range of from about 15 to 300 MPa, more preferably within a range of from about 20 to 150 MPa, more especially 20 to 45 MPa.

c. The core of the tubing wall provides at least a slight majority of the wall thickness relative to any other single layer. The core includes the inner layer of the wall as well as any other layers composed at least of the first thermoplastic polymer. More specifically, the thickness ratio of the wall layers incorporating first thermoplastic polymer to the wall layers incorporating second, third and additional thermoplastic polymer is about 1:1 to about 30:1, preferably from about 1:1 to about 10:1, more preferably from about 1:1 to about 5:1. This parameter allows the flexibility of the wall core to dominate the composite characteristics of the multilayered tubing.

d. The multilayered tubing preferably exhibits a kink/rekink resistance that mimics or is greater than that of polyvinyl chloride medical tubing. Examples of such medical tubing include those given in foregoing paragraph a. Preferably, the kink/rekink resistance of the tubing is in a range of from about 1.8 or greater, more preferably from about 2.0, especially 2.2 or greater as measured by the kink-o-meter test described in the following examples section. Although relation to the kink/rekink of medical PVC tubing is referenced, the invention includes application of the multilayer tubing to non-medical tubing uses needing a similar resistance function.

e. In addition to the flexibility of the first thermoplastic polymer and the core of the tubing wall, the multilayered tubing itself preferably exhibits a flexibility that mimics or is greater than that of polyvinyl chloride medical tubing. Examples of such medical tubing include those given in foregoing paragraph a. More preferably, the multilayered tubing has a Young's modulus within a range of about 15 to about 60 MPa. Although relation to the kink/rekink of PVC medical tubing is referenced, the invention includes application of the multilayer tubing to non-medical tubing uses needing a similar resistance function.

f. The multilayered tubing preferably exhibits a tensile strength that is lower than that of polyvinyl chloride medical tubing but not so low as to deform to constrict the bore when pulled at both tubing ends by medical personnel. (See the values of stress at 50% strain in Examples 1–18.) To compensate for lower tensile strength, the tubing can be made with thicker walls. Tubing samples have been tested with the pinch and roller clamps used in standard polyvinyl chloride IV sets and by nurses and found to be of sufficient strength for typical medical use.

g. The outside surface layer of the tubing wall and in preferred embodiments, the multilayered tubing itself preferably exhibits an abrasion resistance that mimics or is greater than that of polyvinyl chloride medical tubing. Examples of such medical tubing include those given in foregoing paragraph a. More specifically, the outside surface layer of the tubing wall and preferably, the multilayered tubing itself exhibits an outside surface abrasion resistance within an abrasive index range of about 100 or greater as measured by ASTM test D1630-83, standard test method for rubber property-abrasion resistance (NBS abrader). Although relation to the abrasion resistance of PVC medical tubing is referenced, the invention includes application of the multilayer tubing to non-medical tubing uses needing a similar resistance function.

h. The multilayered tubing preferably exhibits essentially complete resiliency and essentially no wall failure throughout at least a 45 hour period of a simple Clamp Test as described in the Tubing Clamp Test in the Examples. Such a resiliency includes an ability of the tubing wall to be completely collapsed without suffering permanent distortion. The wall should return to its original state to show essentially complete resiliency. It should not crack or exhibit signs of stress weakening to show essentially no wall failure.

The kink/rekink resistance of the multilayered tubing is an important physical characteristic. Resistance to kinking is the ability of the tubing to resist the tendency, upon bending, to form a cross-sectional crease in the tubing wall. Such a crease could completely or partially shut off or occlude fluid flow in the bore of the tubing. The resistance toward rekink is the ability of the tubing to resist a tendency to reform a crease in the wall after having been kinked. The kink/rekink resistance of tubing can be tested with a "Kink-O-Meter" as described in the Kink Test Protocol and Examples 1–18 and depicted in FIGS. 3A, 3B and 3C.

Generally, the multilayered tubing of the invention will exhibit a kink/rekink characteristic between that of the individual layers of the wall as would be expected. However, preferred embodiments of the multilayered tubing have an unexpected kink/rekink resistance. These embodiments exhibit a kink/rekink resistance which is significantly better than that of the individual layers. For example, a multilayered tubing made of an inner layer of a copolymer of ethylene and butene (such as an "Exact" polymer manufactured by Exxon Corp of Houston, Tex.) and an outside surface layer of an ionomeric copolymer of ethylene and methacrylic acid with zinc or sodium ions (such as a "Surlyn" polymer manufactured by the DuPont Co. of Wilmington, Del.) displays surprising kink/rekink resistance characteristics relative to single layer tubings of the same dimension and the individual polymers. Further details about these test results are provided in the "comments" about Examples 1–18.

The multilayered tubing is capable of bonding to itself and to other plastics through the use of adhesives such as cyanoacrylates and epoxies, solvent welding, radio frequency welding, microwave welding especially through the use of susceptor particles and thermal welding. The multilayered tubing is sterilizable through gamma irradiation and ethylene oxide. It preferably does not degrade under such sterilizing conditions. The multilayered tubing resists oxidative and ultraviolet degradation such that in a preferred embodiment, it has a significantly long shelf life and does not turn yellow or age like polyvinyl chloride.

First Thermoplastic Polymer

The first thermoplastic polymer is used to form the inner layer serving as the core of the tubing wall. It includes any soft conformable thermoplastic polymer having the characteristics, flexibility and preferably the Young's modulus described above. Preferred thermoplastics include polymers of a C2 to C4 mono-unsaturated alkene, copolymers of a majority of a C2 to C4 mono-unsaturated alkene with a minority of a substituted olefin monomer such as C4 to C14 mono-unsaturated alkene or a C8 to C14 aryl alkene, and copolymers of a majority of a C2 to C4 mono-unsaturated alkene with a minority of a substituted C2 to C6 mono-unsaturated alkene having a substituent such as C1 to C6 alkoxy carbonyl, carboxylic acid, carboxamide and carboxylic ester groups. Examples include copolymers of olefins such as ethylene and propylene with substituted olefins such as vinyl acetate (EVA or PVA), N-methyl acrylamide (EAM or PAM), acrylic acid (EAA or PAA), methacrylic acid (EMA and PMA), EMA or PMA ionomers (EMAZ or PMAZ with zinc; EMAS or PMAS with sodium) and acrylate and methacrylic esters having C1 to C6 alkyl groups. In the case of the copolymer of PVA, the acetate can be partially or wholly hydrolyzed to yield polyvinyl alcohol (PVO). Examples as well include ethylene or propylene copolymers of all hydrocarbon substituted olefins such as ethylene or propylene and styrene (ES or PS), ethylene or propylene and butene (EB or PB) and ethylene or propylene and octene (EO or PO). Particular examples include copolymers of ethylene and vinyl acetate (EVA), ethylene and butene (EB), ethylene and n-butyl acrylate (EBA), and ethylene and ethyl acrylate (EEA).

Generally, as the amount of substituted olefin monomer or alkyl or aryl olefin monomer is increased in such an olefin copolymer, the Young's modulus of the copolymer will decrease. Consequently, the ratio of majority olefin monomer to minority substituted olefin monomer in the copolymer will be selected so that the copolymer will have the appropriate Young's modulus as described above. Preferably, this amount is from about 2% to about 50%, especially preferably about 10% to about 40% on a weight basis.

Second and Third Thermoplastic Polymers

The second and third thermoplastic polymers include any tough, abrasion resistant thermoplastic polymer having the characteristics and the high Young's modulus described above. The second and third thermoplastic polymers can have any suitable backbone structure such as cross-linking, pseudo-cross-linking, backbone branching, randomization, grafting, ionomeric linking, a combination of crystalline and amorphous domains, hydrogen bonding, and backbone structures that restrict the degrees of three dimensional movement of the backbone. By selecting an appropriate backbone character, the degree of substitution on the monomers and the amount of minor monomer present, a tensile strength, Young's modulus and abrasion resistance suitable for the tubing can be obtained. Generally the second and third thermoplastic polymers have the same characteristics but are not necessarily of the same chemical structure. Preferably, the second and third thermoplastic polymers include polyolefins, cross-linked polyolefins, olefin-substituted olefin copolymers as well as polyurethanes, polyethers, and polyesters.

The olefinic monomers used alone or in combination to form the polyolefins can be selected from aliphatic and aromatic olefins of two to fourteen carbons such as ethylene, propylene, butene, octene and styrene. Preferred polymers and copolymers of such olefins include polyethylene, polypropylene, copolymers of ethylene and butene (EB) and copolymers of ethylene and styrene (ES). In copolymers of olefins, the minor olefin monomer (C4 to C14) preferably is present in a range of from about 2% to about 20% on a weight basis.

When a copolymer is used for the second or third thermoplastic polymer, it can also be formed of a C2 to C4 olefin monomer and a substituted olefinic monomer selected from C2 to C6 mono-unsaturated olefins having such substituents as oxyalkanoyl, carboxyl, carboxamido and other similar polar groups. Examples include acrylic acid, methacrylic acid, acrylamide and similar hydrogen bonding or cross-linkable olefins.

The backbone structures degree of substitution and amount of minor monomer present is mentioned above for the second and third thermoplastic polymers will be selected so as to preserve the thermoplastic character of the polymer and to provide the degree of abrasion resistance, toughness and stiffness meeting the Young's modulus requirement described above. Moreover, the thermoplastic olefin copolymers are selected for use as second and third thermoplastic polymers according to the guidelines given above for variation of Young's modulus. Preferred olefin copolymers include a majority of C2 to C4 olefin monomer and a minority of substituted olefin monomer. Preferably, the amount of minority monomer present is from about 2% to about 40%, preferably about 2% to about 20% on a weight basis. The higher amount of minority monomer in such copolymer makes the copolymer stiffer and tougher.

Preferred First, Second and Third Thermoplastic Polymers

In preferred embodiments, the first, second and third chlorine-free thermoplastic polymers are all olefinic polymers. Examples of preferred first thermoplastic olefinic polymers include ethylene-vinyl acetate copolymers (EVA), ethylene alkyl acrylate copolymers such as ethylene n-butyl acrylate copolymers (EBA), ethylene-butene copolymers (EB), ethylene-octene copolymers (EO) and combinations thereof. The EVA copolymers (such as the ULTRATHENE copolymer manufactured by Quantum Chemical Corp., New York, N.Y. and EB copolymers (such as the Exact copolymer manufactured by the Exxon Chemical Company, Houston, Tex.) are particularly preferred. Nonlimiting examples of second and third thermoplastic olefinic polymers include ethylene acrylic acid copolymer (EAA such as Nucrel™ copolymer manufactured by the DuPont Co., Wilmington, Del.) and ionomeric ethylene-methacrylic acid copolymer with zinc or sodium (EMAZ and EMAS such as Surlyn™ copolymers manufactured by the E. I. Du Pont de Nemours and Co., Wilmington, Del.).

The first, second and third thermoplastic polymers may also constitute olefin copolymers of the same two monomers but with differing ratios of those monomers. That differing ratio changes the modulus value of the resulting copolymer and hence makes the copolymer a first, second and third thermoplastic polymer. For example, the first, second and third thermoplastic polymers can all be obtained from EVA and EBA copolymers by altering the percent by weight content of vinyl acetate (VA) and n-butyl acrylate (n-BA) monomers, respectively, in those EVA and EBA copolymers. EVA and EBA copolymers with relatively high VA and n-BA contents provide low Young's modulus materials suitable for use in the inner layer of the multilayered tubing. On the other hand, EVA and EBA copolymers with relatively low VA and n-BA contents provide high Young's modulus materials suitable for use in the outside surface layer and, for a tubing of three or more layers, the inside surface layer. For example, when an EBA copolymer composes the inner layer and the outside and inside surface layers, its n-BA content is preferably from about 15 to 30% for the inner layer, and preferably from about 1% to about 20%, more preferably from about 1% to about 15%, and most preferably from about 2% to about 10% for the surface layers, the percentage being on a molar basis. In another example the inner layer of a three layer wall is an EVA copolymer with a VA content of from about 15% to about 40% VA, while the outside and inside surface layers are EVA copolymer with a VA content of from about 1% to about 20% VA on a weight basis. Alternatively, the outside surface layer of that wall can be an EVA copolymer with a VA content of from about 1% to about 20% VA, while the inside surface layer of that wall can be an EVA copolymer with a VA content of from about 15% to about 40% percent VA on a weight basis.

Dimensions

The diameter of the multilayered tubing and its wall thickness will vary depending upon the intended use, and thus, can readily be selected by those skilled in the art. Generally, the inside diameter of the tubing will range from about 0.25 mm to about 38 mm, preferably about 0.4 mm to about 12.7 mm, more preferably about 0.8 mm to about 6.4 mm. Wall thickness will range from about 0.25 mm to about 12.7 mm, preferably about 0.4 mm to about 9.5 mm. The large size tubing finds general use in non-medical, fluid carrying applications such as plumbing, ultrapure fluid and gas transport and the like. The smaller size tubing finds general use in medical applications such as IV sets, infusion pump sets, catheters, medical fluid lines and the like as given above in the paragraphs on tubing parameters. For smaller bore tubing such as tubing of outside diameter of 4.3 mm, which typically is used in IV therapy sets, it is preferred to use an OD/ID ratio of 1.40 or greater. It is most preferred to use OD/ID ratios of 1.50 or greater. Using these ratios and the copolymers described in Examples 1–18 resulted in kink/rekink resistance higher than that of polyvinyl chloride tubing.

As generally explained above, the layer or layers forming the flexible core of the tubing wall will be slightly to significantly larger in thickness than any other single tough layer of the wall. This factor allows the core characteristics of the wall to dominate the characteristics of the tubing. In a preferred embodiment, the outside surface layer and for a tubing of three or more layers, the inside surface layer, are thin protective coverings for the core of the wall. In particular, the increased hardness and toughness of the second and third thermoplastic polymers allows them to be coextruded as substantially thinner layers, and yet still provide adequate tensile strength to the tubing and adequate protection for the flexible core of first thermoplastic polymer.

Generally, any ratio of inner layer or layers to outside surface layer, and for a wall configuration of three layers or more, any ratio of inner layer or layers to outside and inside surface layers, will suffice as long as it provides adequate tensile strength to the tubing and adequate protection of the wall core of first thermoplastic polymer. Numeric parameters are as given above in paragraph c of the parameters section.

In a preferred embodiment, when using the preferred EVA or EB and EMAZ or EMAS ionomeric copolymers to form a two-layer or three-layer tubing according to the present invention, the inner layer is preferably from about 200µ to about 1200µ, more preferably from about 200µ to about 1000µ, and most preferably from about 200µ to about 600µ thick, while the outside and inside surface layers are preferably from about 10µ to about 800µ, more preferably from about 50µ to about 600µ, and most preferably from about 50µ to about 200µ thick.

Thermoplastic Polymer Modulus Measurement

The stiffness/flexibility of a given thermoplastic polymer is conveniently measured and expressed in terms of the Young's modulus, as reported in megapascals (MPa), for the polymer. A polymer with a low Young's modulus (e.g., from about 2 MPa to about 60 MPa) is soft and flexible while a polymer with higher Young's modulus values (e.g., from about 15 MPa to about 300 MPa) is relatively stiff and inflexible. The low Young's modulus polymers also tend to be more easily cut or physically abraded and serve as the first thermoplastic polymer. Conversely, the high Young's modulus polymers present a relatively hard, tough (i.e., cut and scratch-resistant) surface and serve as the second and/or third thermoplastic polymers.

The measurement of Young's modulus follows the procedure outlined by the reference guide for "Instron Series IX Automated Materials Testing System" Version 5, Instron Company, Canton, Mass.; pp 13–19 to 13–27; Issue B, November, 1990 or by the operator's guide for "MTS Sintech TestWorks™ Advanced Software for Materials Testing", Version 2.1; MTS Systems Corp., Eden Prairie, Minn.; pp B-10 to B-12; November, 1992 incorporated herein by reference. The following examples section provides the details for such measurements as applied to multilayered tubing. The functional and numeric parameters for abrasive-resistance and flexibility of the first, second and third thermoplastic polymers used in the wall of the multilayered tubing are related to, and in preferred embodiments, are indicated by the Young's modulus of these polymers. Those parameters are given above in the parameters section.

Tie Layer and Optional Additives

While it is preferable not to utilize a tie layer or layers in the wall of the multilayered tubing to bond the various layers together, there may be multilayered constructions in which such layers are desired. When a tie layer is employed, it can be composed of materials which provide structural integrity to the multilayered constructions, without substantially affecting the other desirable characteristics of the multilayered tubing, such as flexibility, clarity and environmental-compatibility. The selection of the particular tie layer material to be utilized in multilayered tubing according to the present invention can be made from the wide variety of available tie layer materials and is subject to the particular needs and preferences of those skilled in the art. Preferred tie layer polymers include coextrudable adhesive resins such as "BYNEL™ resin" manufactured by E. I. Du Pont de Nemours and Co. of Wilmington, Del.; "ADMER™ resin" manufactured by Mitsui Plastics, Inc. of White Plains, N.Y.; "Plexar™ resin" manufactured by Quantum Chemical Corp. of Rolling Meadows, Ill.; and "PRIMACOR™ polymer" manufactured by Dow Chemical Co. of Midland, Mich.

To provide specific additional characteristics to multilayered tubing of the present invention, the outside surface layer and/or the inner layer can also contain conventional non-leachable additives, such as antistatic materials, pigments, dyes, ultraviolet absorbers, nucleating agents, quenching agents and the like. For example, UV absorbers can be added to one or more of the layers of the wall of the multilayered tubing for application in IV sets used with light-sensitive drugs.

Methods of Preparation

The preferred method of preparing multilayered tubing according to the present invention is coextrusion. Coextrusion brings diverse polymeric materials together to form a unitary layered structure, such as tubing. This allows for unique combinations of materials, and for structures with multiple functions, such as toughness and flexibility as well as environmental and medical compatibility.

Component polymeric materials according to the present invention can be coextruded from the melt state in any shape, according to the intended end use thereof. The shape and/or thickness of the coextruded structure will be dependent upon the efficiency of the particular extrusion equipment utilized. Generally, tubes having a circular cross-section, a bore and a wall with inside and outside surfaces are the preferred coextruded structures. Where appropriate, the multilayered tubing according to the present invention can be uniaxially, biaxially or multiaxially oriented to further enhance its physical characteristics.

For example, in a preferred construction, a multilayered tubing according to the present invention is composed of a two-layered, coextruded tubing of at least an inner layer of an EVA copolymer with a VA content of about 28%, and at least an outside surface layer of an ethylene-methacrylic acid, zinc or sodium ionomeric copolymer that is coextruded along with the inner layer to form an outer protective coating of the multilayered tubing. Another preferred multilayered tubing according to the present invention includes a three-layered tubing with an inner layer of an EVA copolymer containing 28% VA coextruded between outside and inside surface layers of a ionomeric ethylene-methacrylic acid, zinc or sodium copolymers. Also, such a three-layered tubing in which the outside and inside surface layers are composed of an ethylene copolymer can be prepared.

Generally the conditions of coextrusion include use of sufficient heat and pressure to cause each thermoplastic polymer or polymer mixture to melt. Upon transport through the coextrusion die, the united layers of plasticized or melted polymer or polymer mixture are cooled such as by a water bath or air to congeal them into solid multilayered tubing. A stream of cool gas or fluid can be passed through the bore of the hot coextruded tubing to keep the tubing from collapsing. Generally, polymers or polymer mixtures of differing melt temperatures can be used according to the invention. The temperatures of those phases for one polymeric layer should not exceed the decomposition temperature of another polymeric layer, however.

The conditions of coextrusion can also include techniques to orient the tubing layers. The orientation preferably but not necessarily provides additional tensile strength to the tubing. In particular the technique to orient is accomplished by stretching the tubing. Shortly or immediately after the tubing exits the die, a tension force can be applied to the formed tubing to stretch it. The stretching force can be applied by the rate of rolling up the finished, quenched tubing; by the rate at which the tubing is pulled through the quench or cooling fluid; or by the rate at which the tubing is pulled from the coextrusion die. The stretching tension is believed to orient the polymer chains in the direction of the applied force. The orientation or alignment of polymer chains is believed to be the basis for the added tensile strength of the various oriented layers of the multilayered tubing. The orientation technique can also be used to form very small diameter tubes such as those that cannot be directly formed through use of a coextrusion die.

Preferred Embodiments

Figure 2:
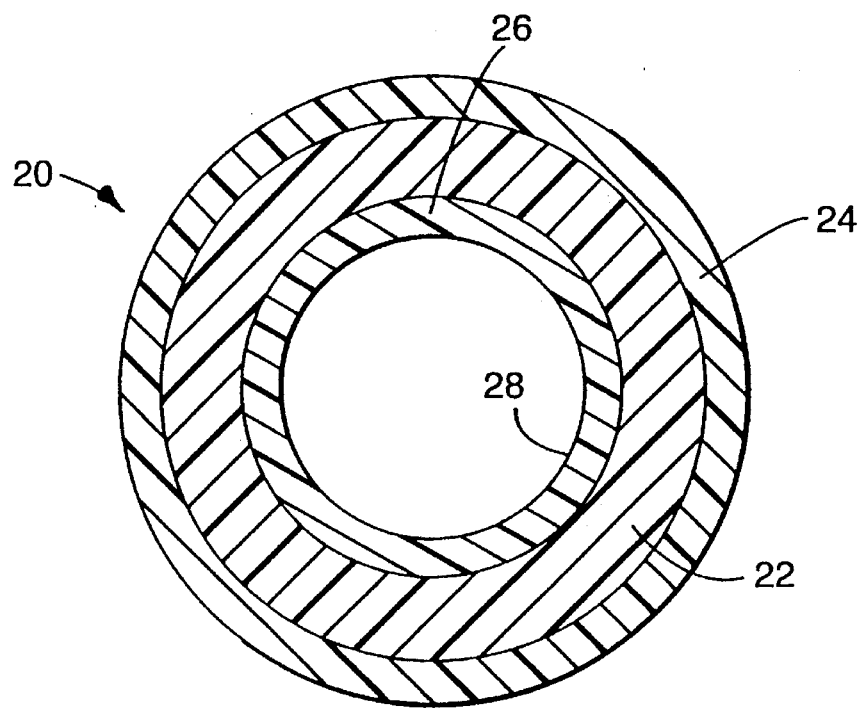
FIG. 2 is a cross-sectional illustration of a second embodiment of a multilayered tubing of three layered wall construction.

FIGS. 1 and 2 show cross-sectional illustrations of two alternative embodiments of multilayered tubings 10 and 20 according to the present invention. FIG. 1 shows a first embodiment of multilayered tubing 10 having a bore 16, an inner layer 12 of a chlorine-free first thermoplastic polymer overlayed by an outside surface layer 14 of a chlorine-free second thermoplastic polymer. The first thermoplastic polymer is substantially softer than the second thermoplastic polymer used in multilayered tubing 10. Thus, the outside surface layer 14 provides a tough, protective coating for the softer, inner layer 12. The Young's modulus of the first thermoplastic polymer is less than that of a polyvinyl chloride tubing used for an IV set, preferably in the range of about 2 to about 30 MPa (megaPascals). The Young's modulus of the second thermoplastic polymer is higher than but not more than about fifteen times the Young's modulus of the first thermoplastic polymer, preferably in the range of about 15 to about 60 MPa.

FIG. 2 shows a second embodiment of multilayered tubing 20 according to the present invention. This embodiment includes a bore 28, inner layer 22 of a chlorine-free first thermoplastic polymer sandwiched between an outside surface layer 24 of a chlorine-free second thermoplastic polymer and an inside surface layer 26 of a chlorine-free third thermoplastic polymer. In this regard, it will be appreciated that outside and inside surface layers 24 and 26 of multilayered tubing 20 can be the same chlorine-free thermoplastic polymer. Alternatively, the inside and outside surface layers can be different types and/or chemical compositions of tough chlorine-free thermoplastic polymer. The inside surface layer 26 of multilayered tubing 20 provides an additional protective coating to the substantially softer inner layer 22 of multilayered tubing 20.

Although they are not shown, tubing embodiments having walls of four and five layers are also preferred. The four layer wall is configured by including a light impervious layer of second or third thermoplastic polymer and colorant between the outside surface layer and the inner layer of the wall configuration illustrated by FIG. 2. This layer will act to prevent light from destabilizing a sensitive chemical fluid being carried by such a multilayered tubing. The tubing embodiment having a five layer wall is configured by inclusion of a dividing layer within the inner layer of first thermoplastic polymer of the wall configuration illustrated by FIG. 2. The dividing layer of this configuration stabilizes the layers of first thermoplastic polymer.

In the particularly preferred embodiment depicted by FIGS. 1 and 2, the inner layer is composed of an EVA copolymer and/or an EB copolymer (such as the EB copolymer trademarked as Exact and manufactured by the Exxon Co. of Houston, Tex.). The outside and inside surface layers are composed of an EMAZ or EMAS copolymer (such as the EMAZ and EMAS copolymers trademarked as SURYLN and manufactured by the DuPont Co., Wilmington, Del.). For example, the inner layer of the multilayered tubing 10 (FIG. 1) can comprise about 0.45 mm–0.8 mm of an EVA copolymer with about a 15–40% VA content or an EB copolymer with about a 15 to 25% content of butene, while second layer 14 can comprise 0.15–0.2 mm of an EMAZ or EMAS copolymer. A soft flexible, and kink/rekink-resistant bi-layered tubing 10 or trilayered tubing 20, with a hard, tough, scratch-resistant protective coating is obtained.

Utility of the Invention

Multilayered tubing according to the present invention can be utilized in a wide range of both medical and non-medical products. In the medical area the multilayer tubing is suitable for replacing chlorine-containing PVC tubing, such as is utilized with intravenous (IV) fluid administration sets, arthroscopy fluid control systems, cardiovascular systems and blood gas monitoring systems, coronary artery bypass tubes, infusion pump tubes, catheters, dialysis tubes, peritoneal lavage tubes, respiratory tubes, endotracheal tubes, gastric feeding tubes, wound drainage tubes, urinary catheter tubes, angioplasty tubes and general purpose PVC tubing such as "Tygon™" brand PVC tubing manufactured by Norton Performance Plastic, Wayne, N.J. When the wall of the multilayer tubing has a core and surfaces composed of chlorine-free thermoplastic polymer which does not swell or form microporous matrices, the tubing will not absorb drug or medical fluids, nor will it contaminate the drug or medical fluid with leachable additive, plasticizer and the like through extraction, exudation or blooming.

The invention has been fully set forth in the foregoing general specification. The following examples are provided to further illustrate the invention. They are not meant to indicate limitations of the broad scope of the invention, however.

Protocols for Physical Measurements

The following discussion provides the general protocols for performing certain physical measurements of tubing prepared according to the invention.

Measurement of Outside Diameter(OD)/Inside Diameter(ID) and Layer Thicknesses

An optical comparator (Nikon Profile Projector Model V-12 with a Nikon SC-102 digital readout scanner) is used to measure tubing diameters and layer thicknesses for multilayered tubing. Relative layer thickness is calculated by assuming the total thickness of the layers is equal to 100%.

Young's Modulusus, Percent Strain at Yield, Load at Fifty Percent Strain, Stress at Fifty Percent Strain and Percent Recovery After Fifty Percent Strain Tensile/elongation measurements are made on tubing samples using a Material Test System (MTS) 880 (MTS Systems Corporation, Eden Prairie, Minn.) with an MTS Sintech Testworks II Application Software Package, version 2.1. ASTM Test Method D876-90 "Standard Test Methods for Nonrigid Vinyl Chloride Polymer Tubing Used for Electrical Insulation" was modified to test the tubing samples. The gauge length of the gripping jaws of the MTS testing machine is initially set 5.08 cm (2 inches) apart. The rate of elongation is 15.24 cm (6 inches) per minute. For each tubing sample, three replicates are run. For each replicate the following information is computed and averaged:
1. Young's modulus, computed as the maximum slope of the stress/strain curve, using a 3% strain segment length, see the MTS Sintech Softward Package cited above.
2. Load at 50% strain
3. Stress at 50% strain In addition to the measurements listed above, a measurement is made of percent recovery in length after 50% strain. The tubing samples were stretched to 50% strain, allowed to relax for one minute without a load, and stretched again until a reading indicating a load of 0.045 kgf (0.1 lb) is obtained. The distance the gripping jaw travels in order to reach this reading is recorded as a percent of the original length 5.08 cm (2 in). Percent recovery is calculated as 100% minus the percent of increase in length. For example, if the tubing sample returned to 107% of its original length, that is recorded as 93% recovery.

Since stress/strain characteristics can change over time after extrusion, measurements are reported after at least one month following extrusion unless otherwise stated.

Kink/Rekink Resistance Test Method

Figure 3A:
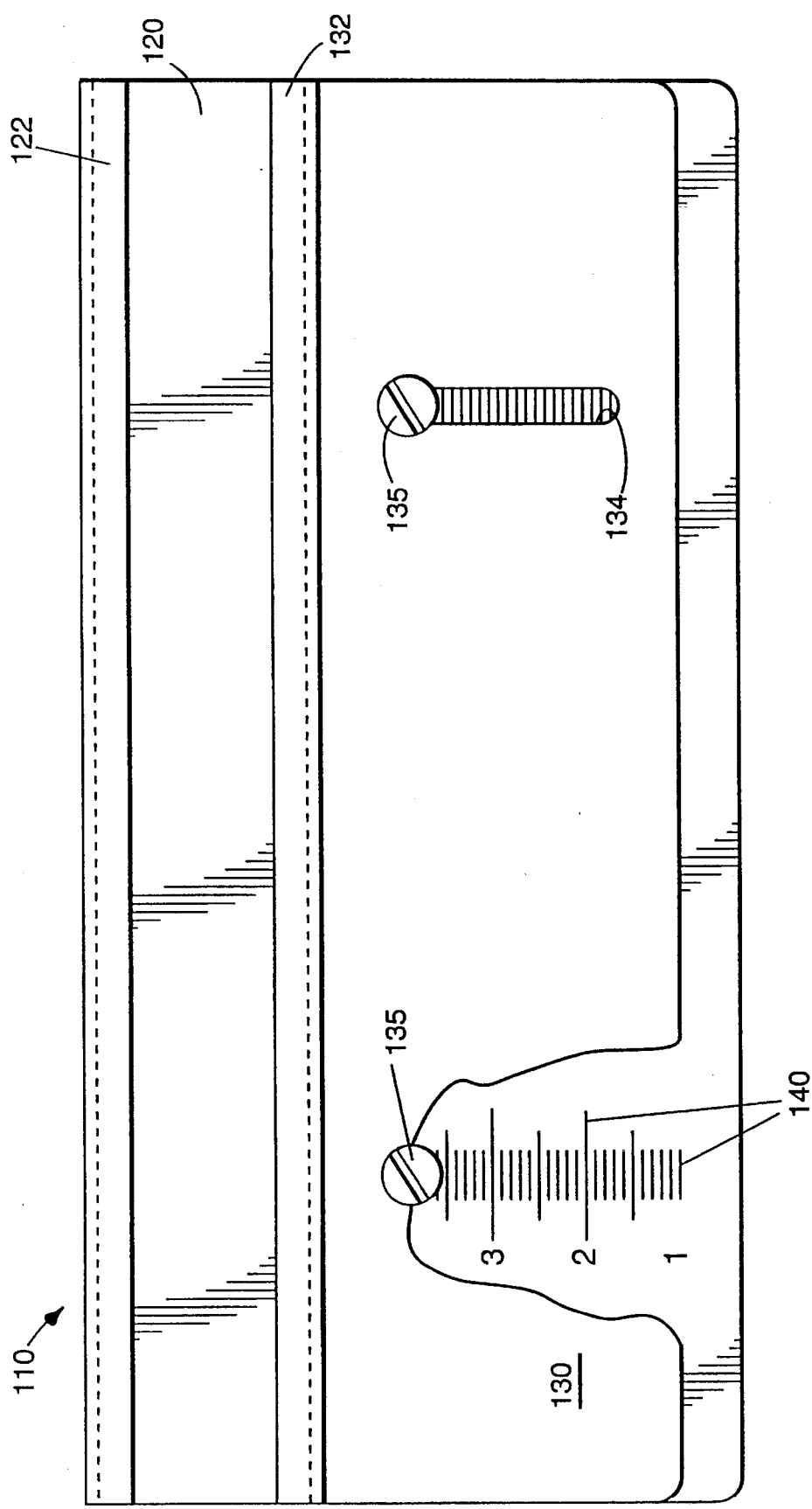
FIG. 3A is a front planar view of a "Kink-O-Meter".
Figure 3B:
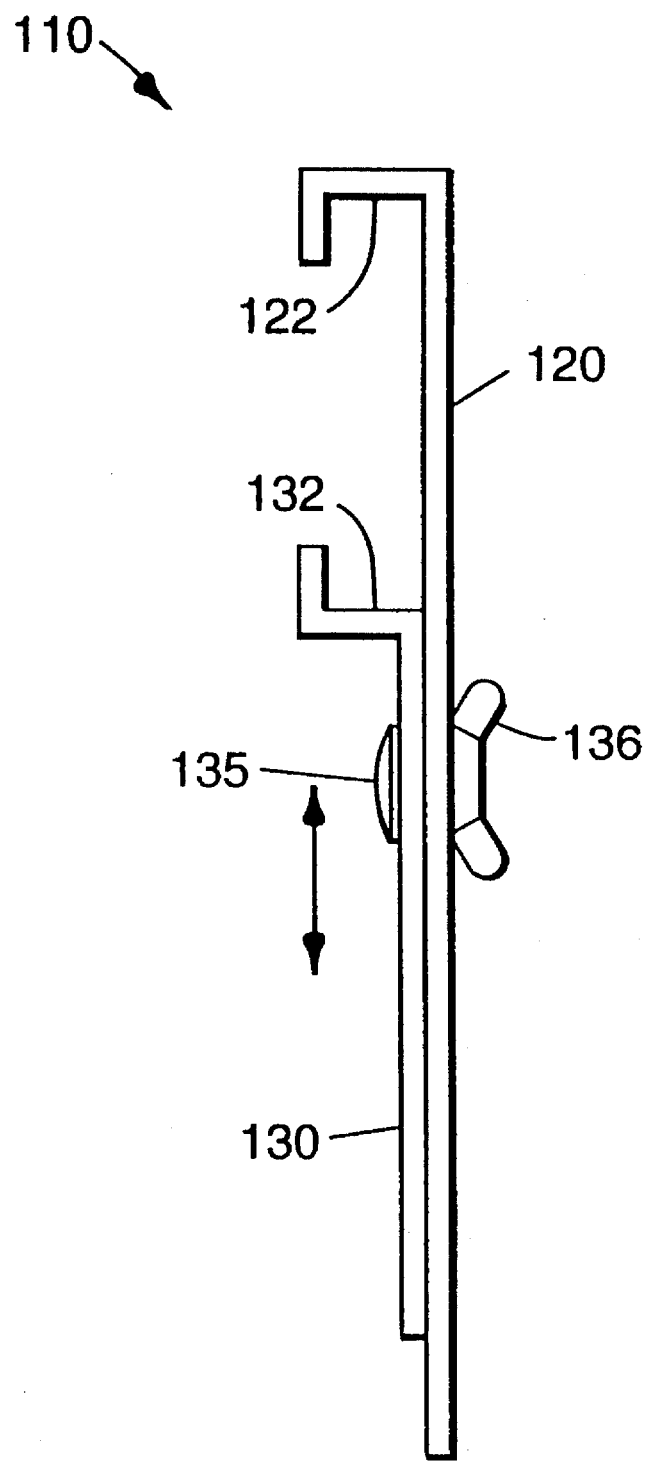
FIG. 3B is a side planar view of a "Kink-O-Meter".

The Kink/Rekink Resistance Test Method is used to determine the resistance of a tubing sample to a sudden buckling collapse which seals off the lumen of the tubing sample when the sample is bent back towards itself over too small a radius. Once such a collapse (hereafter called a kink) has occurred in a polymeric tubing sample, there typically is a weakened area which is thereafter particularly susceptible to a similar failure (hereafter called a rekink). Rekinking can occur at a larger tubing bend radius than is required to cause the original kink. In particular, during typical IV therapy it is conventional to loop the IV tubing 180 degrees and tape the loop to a patient's wrist. A possibility of a kink in the IV line in that loop or elsewhere is a recognized complication in delivering IV therapy and must be guarded against by medical practitioners. The method is used to compare the characteristics of flexible tubings with respect to their ability to resist kinking and rekinking. The test is suitable for tubing diameters between 0.127 to 0.635 cm, and the test is conducted at room temperature. Referring now to FIGS. 3A and B, the test is conducted on a test apparatus 110 (Kink-O-Meter) used to measure kink and rekink resistance of a tubing sample. The test apparatus 110 includes a lower plate 120 having a lip 122 along one edge. Two threaded studs 135 are mounted on the lower plate 120. An upper plate 130 having a lip 132 along one edge and two slots 134 is mounted in sliding engagement with lower plate 120 with the threaded studs 135 fitting into the two slots 134 in such a way that the lips 122 and 132 are aligned parallel to each other. A pair of wing nuts 136 (FIG. 3B) are mounted on the threaded studs to provide a convenient amount of sliding resistance between the lower plate 120 and the upper plate 130. Indicia 140, which are read against the edge of the upper plate 130, are provided on lower plate 120 in order to quantify the results. The indicia 140 numbers range from 3.4 when the lips of the plates are fully closed (i.e., separated by a distance of 1.27 cm) to 1.2 when the lips of the plates are fully open (i.e., separated by a distance of 3.8 cm).

Figure 3C:
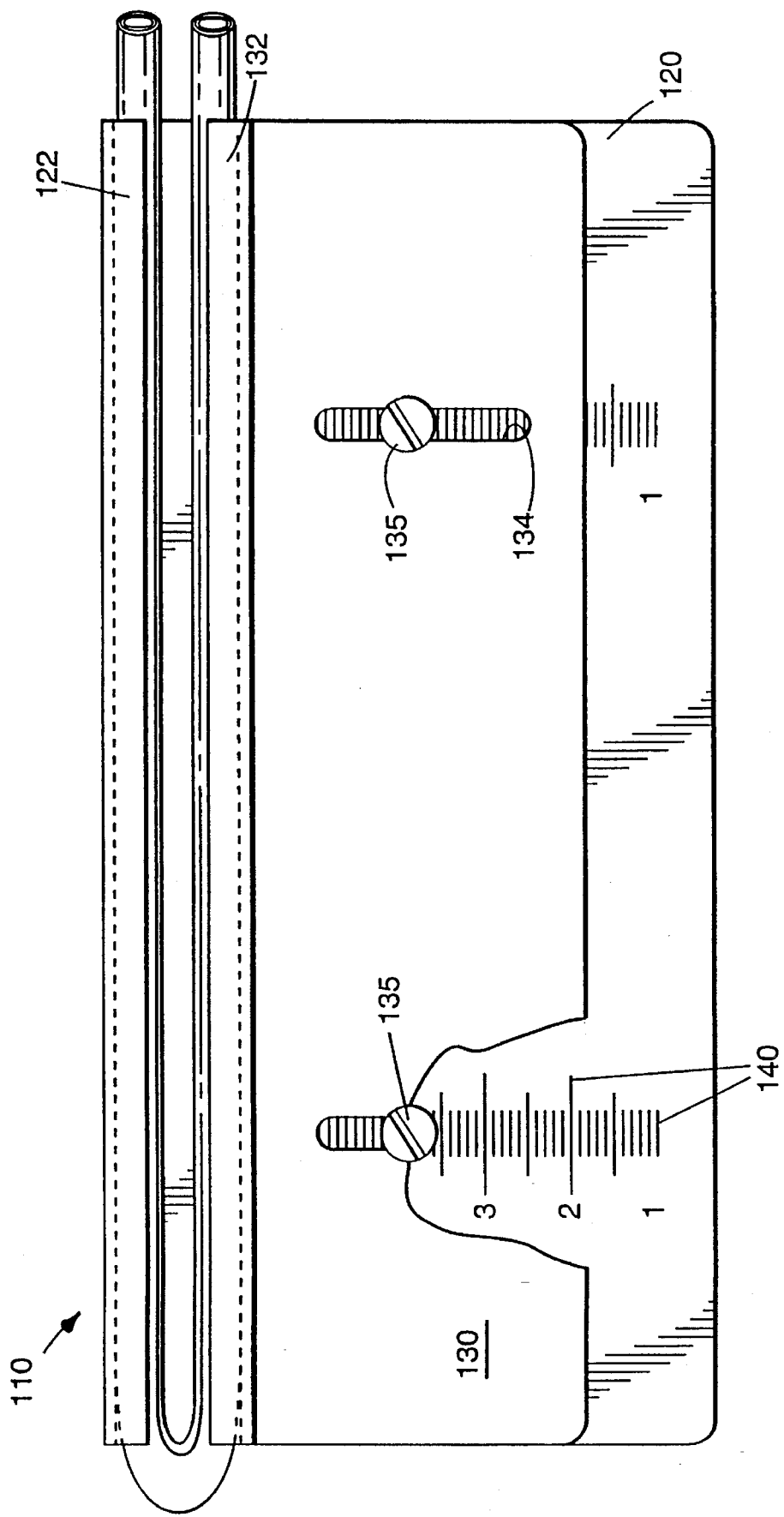
FIG. 3C is a front planar view of a "Kink-O-Meter" in use.

The procedure for determining kink and rekink resistance with the Kink-O-Meter is as follows:
1. Cut a tubing sample at least 30 cm long.
2. Move the upper plate on the test apparatus until the trough formed between the lip of the upper plate and the lip of the lower plate is fully open.
3. Curl the tubing sample into a "U" shape and place it into the trough as illustrated in FIG. 3C.
4. Slowly slide the upper plate to decrease the width of the trough thus decreasing the radius of curvature of the tubing sample until the tubing sample kinks. The rate of sliding should be slow and uniform, at a rate which will take 10 to 15 seconds from the opened position to the closed position.
5. Reading the indicia, record the number exposed on the lower plate along the bottom edge of the upper plate which is identified as the "kink number".
6. Mark the tubing sample with ink at the kink location.
7. Remove the tubing sample from the trough and press the sides of the "U" shape tubing sample together to assure full tube kinking.
8. Straighten the tubing sample to open the kink.
9. After 30 seconds, place the tubing sample in the back in the trough so that the kink area is at the bottom of the "U".
10. Repeat step 4 until the tubing sample kinks again.
11. Record the number exposed on the lower plate along the bottom edge of the upper plate which is identified as the "rekink number".

EXAMPLES 1–12

Three-Layer Tubing with EVA and EB Inner Layer

Twelve ABA three-layered tubings composed of an inner layer (B) and outside and inside surface layers (A) were coextruded from a multilayer tubing die with a diameter of 0.737 cm and a 0.635 cm mandrel. The copolymer for the B layer was supplied to the die from a 2.5 cm (1 inch) Killion extruder commercially available as "Killion Model KL-100" from Killion Extruders, Inc., Cedar Grove, N.J., using a conventional screw. The copolymer for the A layers was supplied to the die from a 1.3 cm (½ inch) Randcastle microextruder commercially available from Randcastle Extrusion Systems, Inc., Little Falls, N.J., using a conventional screw. The melt from copolymer A was split into two streams within the die and combined with copolymer B in an ABA configuration prior to exiting the die. The molten, multilayered tubing was then passed immediately into a water bath commercially available as "Killion VT-2-6-1 Model Vacuum Tank" from Killion Extruders, Inc., Cedar Grove, N.J., where the tubing was quenched and solidified. To prevent collapse of the tubing in its molten state, air was fed to the inside of the tubing (bore) through a small hole in the center pin of the die. The internal die configuration was varied and the speeds of the extruder screws were adjusted to obtain the desired relative layer thicknesses. The rate per minute (RPM) of the extruder screw was held constant for the inner layer while the RPM was varied over the range shown in Table 1. The tubing was pulled from the die and through the water baths by a constant speed belt puller commercially available as "Killion Model 2-12" from Killion Extruders, Inc., Cedar Groves, N.J. By adjusting the ratio of puller speed to the overall output of the die, and by adjusting the air pressure in the lumen of the tube, the outside and inside diameter of the tubing was controlled. Specific extruder conditions for Examples 1–12 are shown in Table 1.

The A layers of each of the tubings of Examples 1–3 and 7–9 were comprised of a very low modulus, ethylene/ methacrylic acid copolymer sodium doped ionomer resin (EMAS) commercially available as "Surlyn™ resin No. 8320" from E.I. Du Pont de Nemours and Company, Wilmington, Del.. The A layers of each of the tubings of Examples 4–6 and 10–12 were comprised of a very low modulus, ethylene/methacrylic acid copolymer zinc doped ionomer resin (EMAZ) commercially available as "Surlyn™ resin No. 9320" from E.I. Du Pont de Nemours and Company, Wilmington, Del.

The B layer of each of the tubings of Examples 1–6 was comprised of an EVA copolymer with a 28% by weight VA content commercially available as "Ultrathene™ resin No. UE 645-04" from Quantum Chemical Co., Rolling Meadows, Ill. The B layer of each of the tubings of Examples 7–12 was comprised of an ethylene/butene (EB) copolymer commercially available as "Exact™ resin No. 4028" from Exxon Chemical Co., Houston, Tex.

Individual layer thicknesses, relative layer thickness, outside diameter, inside diameter, load at 50% strain, stress at 50% strain, Young's modulus, recovery from 50% strain and kink/rekink resistance of the three-layered example tubings were determined by using the test methods described above. The results are shown in Table 2.

COMPARATIVE EXAMPLE A

Single layer polyvinyl chloride tubing from an IV set commercially available as "3M Healthcare-Model 230 IV Set" from 3M, St. Paul, Minn. was measured using the test methods described above for outside diameter, inside diameter, load at 50% Strain, stress at 50% Strain, Young's modulus, recovery From 50% Strain, and kink/rekink resistance. The results are shown in Table 2.

COMPARATIVE EXAMPLES B–E

A series of four single-layer extruded tubing constructions were made from ethylene/butene copolymers, ethylene/methacrylic acid ionomer copolymer resins and ethylene/vinyl acetate copolymers. Specific copolymer resins employed, included: (B) an ethylene/vinyl acetate (EVA) copolymer with 28% vinyl acetate units commercially available as "Ultrathene™ UE 645-04" from Quantum Chemical Corp., Rolling Meadows, Ill.; (C) an ethylene/methacrylic acid sodium doped ionomer resin (EMAS) commercially available as "Surlyn™ resin No. 8320" from E.I. Du Pont de Nemours and Company, Wilmington, Del.; (D) an ethylene/methacrylic acid zinc doped ionomer resin (EMAZ) commercially available as "Surlyn™ resin No. 9320" from E.I. Du Pont de Nemours and Company, Wilmington, Del.; (E) an ethylene/butene copolymer (EB) commercially available as "Exact™ resin No. 4028" from Exxon Chemical Company, Houston, Tex.

These copolymer resins were extruded into tubing using the 1.3 cm (½ inch) barrel Randcastle microextruder used in Examples 1–12 with the Killion™ extruder turned off. Extruder conditions for the single-layer extruded tubings of Comparative Examples B–E are shown in Table 1.

Outside diameter, inside diameter, load at 50% strain, stress at 50% strain, Young's modulus, recovery from 50% strain and kink/rekink resistance of the single layer tubings were determined by using the test methods described above. The results are shown in Table 2.

Comments Regarding Examples 1 through 12

The Young's modulus of the three-layered tubing in Examples 1–12 was similar to that of PVC or slightly higher. The low Young's modulus of these tubings indicate that the flexibility was similar to PVC. Generally an increase in the relative layer thickness of the inner and outer layers of the three-layered tubing samples results in an increase in the Young's modulus.

Recovery from 50% strain was at least 90% in Examples 2–3, 5–6, and 7–12. These results compare favorably with PVC and in addition indicate how the tubing would recover from stretching in use.

Strength or stress at 50% strain, while less than that of PVC, is adequate for most medical tubing uses.

ABA three-layered tubing made with the ethylene/methacrylic acid copolymer ionomer resins in the peptide and inside layers and EVA or ethylene/butene copolymer core layers had kink/rekink resistance equal to or greater than tubing made from any copolymer resin in a single layer. By adjusting the layer thicknesses of the ABA three-layered tubings, a tubing which has a greater kink/rekink resistance than PVC was produced. In particular, while the kink/rekink resistance of polyvinyl chloride tubing is 2.5/2.1, the kink/rekink resistance of the multilayered tubing of ionomeric and EB (Surlyn and Exact) polymers is as high as 3.2/3.1.

COMPARATIVE EXAMPLE F

A single layer extruded tubing construction was made from ethylene/methacrylic acid (EMAZ) zinc doped ionomer resin commercially available as "Surlyn™ resin No. AD 8255"; MI=4 g/10 min; from E. I. Du Pont de Nemours and Company, Wilmington, Del. This copolymer resin was extruded into tubing using the 1.3 cm (½ inch) barrel Randcastle microextruder as described in Examples 1–12 with the Killion™ extruder turned off. Extruder conditions for the single-layer extruded tubings of Comparative Example F are shown in Table 3.

Outer diameter, inner diameter, load at 50% strain, Young's modulus, and kink/re-kink resistance were measured using the test methods described above. The results are shown in Table 4.

EXAMPLES 13–18

Three-Layer Tubing with EB Inner Layer

Six ABA three-layered tubings composed of an inner layer (B) and outside and inside surface layers (A) were coextruded from a multilayer tubing die as described for Examples 1–12. The specific extruder conditions for the three-layered coextruded tubings are shown in Table 3.

The A layers of each of the tubings of Examples 13–18 were composed of a low modulus, ethylene/methacrylic acid copolymer zinc doped ionomer resin (EMAZ) commercially available as "Surlyn™ resin No. AD 8255" from E.I. Du Pont de Nemours and Company, Wilmington, Del. The B layer of each of the tubings of Examples 13–18 was comprised of an ethylene/butene copolymer (EB) commercially available as "Exact™ resin No. 4028" from Exxon Chemical Co., Houston, Tex.

Young's modulus for ABA three-layered tubings of Examples 13–17 was predicted using a law of mixtures:

$$P = D_i P_i + X_c P_c + X_o P_o \quad (1)$$

where P is Young's modulus of an ABA three-layered tubing;
$X_i$, $X_c$, $X_o$ are the weight fractions of the inner, core, and outer layers; and $P_i$, $P_c$, $P_o$ are the Young's modulus of the single layer tubing of the same composition.

Young's modulus for the tubing in Examples 13–17 was measured using an "Instron Model 1122" from Instron Company, Canton, Mass., with a software program. The gauge length between the gripper jaws was set at 5.08 cm (2 inches) and the cross head speed was 50.8 cm/minute (20 inches/minute). Young's modulus is defined as the initial slope of the stress/strain curve. Fifty percent load/tensile is defined as the force or tensile strength at 50% elongation.

Individual layer thicknesses, relative layer thickness, outside diameter, inside diameter, and kink/rekink resistance of the three-layered tubings were determined by measuring using the test methods described above. Physical characteristics of Example 18 were determined using the test methods described above using the MTS testing apparatus. The results are shown in Table 4.

Comments Regarding Examples 13 through 18

The results show that Young's modulus could be predicted using the law of mixing in Equation 1. However, the rekink value cannot be predicted using the same law of mixing. The rekink values for the three-layered ABA tubings are higher than either of the single layer tubings of the same composition. In particular, while the kink/rekink resistance of the ionomeric polymer (Surlyn) tubing is 2.3/1.2 and the kink/rekink resistance of the EB (Exact) polymer tubing is 2.4/1.4, the kink/rekink resistance of the multilayered tubing of ionomeric and EB (Surlyn and Exact) polymers is 2.6–2.8/2.0–2.2[1]. Thus, the multilayered tubing surprisingly displays higher kink/rekink resistance than either of the individual polymer layer tubings.

The rekink resistance was tested with a Kink-O-Meter. The rekink resistance test is described in the protocols before Example 1.

EXAMPLES 19–22

Two Layer Tubing

Four, two-layered coextruded tubings were produced using a 2.5 cm barrel Killion™ extruder (Killion Extruders, Inc. of Cedar Grove, N.J.), and a 1.3 cm barrel Randcastle Microtruder™ extruder, (Randcastle Extrusion Systems, Inc. of Little Falls, N.J.). The extruders were secured to a multilayer die with a 0.5 cm center pin, and a 0.5 cm bushing was used in the sizing vacuum tank of the extrusion line. The tubing constructions of Examples 19–22 were made with varied layer thicknesses by adjusting extruder output. Specific extruder conditions for the two-layered tubings of Examples 19–22 are shown in Table 5.

The outside surface of each of the tubings of Examples 19–22 was composed of an ethylene vinyl acetate copolymer (EVA) containing 6% by weight vinyl acetate (VA) (Petrothene™ No. NA 316-138; melt index=1.3 g/10 min.; density= 0.928 g/cc; Quantum Chemical Co., Rolling Meadows, Ill.). The inner layer of the tubing was comprised of an EVA copolymer with a 28% by weight VA content (Ultrathene™ No. UE 645-04; melt index=3 g/10 min.; density=0.95 g/cc; Quantum Chemical Co., Rolling Meadows, Ill.).

Individual layer thicknesses of the two-layered Example tubings were determined by measuring tube cross-sections via optical microscopy. Samples of each of the Example tubings were cut and trimmed, and then embedded in 3M Scotchcast™ brand electrical resin No. 8 (3M, St. Paul, Minn.). The tubings were then cut into 10 micron (µ) thick cross-sections using a microtome. Specimens were placed on a glass slide in immersion oil with a cover slip placed on top. Layer thicknesses were then determined via transmitted bright field optical microscopy. Due to some misalignment of the extruder's die pin, some of the tubing samples were asymmetric. Therefore, average thicknesses for the inner layer, outside surface, and total thickness of each tube were recorded, and are shown in Table 6.

EXAMPLES 23–26

Red Two Layer Tubing

To more effectively visualize the thicknesses of individual layers of two-layered tubing constructions according to the present invention, the four, two-layered coextruded tubings of Examples 23–26 were produced with a red dye incorporated in the outside surface of the tubings. The tubings of Examples 23–26 were coextruded using the same extruders, multilayer die, center pin, and bushing as used in Examples 19–22. As with Examples 19–22, the tubing constructions of Examples 23–26 were made with varied layer thicknesses by adjusting extruder output. Specific extruder conditions for the two-layered tubings of Examples 23–26 are shown in Table 7.

The outside surface of each of the tubings of Examples 19–23 was composed of an ethylene vinyl acetate copolymer (EVA) containing 6% by weight VA (Petrothene™ resin No. NA 316-138; melt index=1.3 g/10 min.; density=0.928 g/cc; Quantum Chemical Co., Rolling Meadows, Ill.), mixed in a 20:1 ratio with CM74052 red polyolefin color concentrate (Quantum Chemical Co., Rolling Meadows, Ill.). The inner layer of the Example tubings was comprised of an EVA copolymer with 28% by weight VA (Ultrathene™ resin No. UE 645-04; melt index =3 g/10 min.; density=0.95 g/cc; Quantum Chemical Co., Rolling Meadows, Ill.), without a dye incorporated therein.

By utilizing red dye in the outside surface of the tubings of Examples 23–26, the two-layered structure of the Example tubings were clearly visible by eye. Individual layer thicknesses of the two-layered tubings of Examples 23–26 were determined by measuring tube cross-sections via optical microscopy according to the procedure outlined in Examples 19–22. Due to some misalignment of the extruder's die pin, some of the tubing samples were asymmetric. Accordingly, average thicknesses for the inner layer, outside surface, and total layer thicknesses in microns (µ) of the Example tubings were recorded, and are shown in Table 8.

COMPARATIVE EXAMPLES G–N

A series of eight, single-layer extruded tubing constructions were made from several different EVA and ethylene n-butyl acrylate (EBA) copolymer resins (Quantum Chemical Company, Rolling Meadows, Ill.). Specific EVA and EBA copolymer resins employed, included: (G) Enathene™ resin No. EA 705-009; 5% n-butyl acrylate (n-BA); melt index (MI)=3 g/10 min.; (H) Enathene™ resin No. EA 719-009; 19% n-BA; MI=0.3 g/10 min.; (I) Petrothene™ resin No. NA 420; 2.5% VA; MI=2.5 g/10 min.; (J) Petrothene™ resin No. NA 316-138; 6% VA; MI=1.3 g/10 min.; (K) Ultrathene™ resin No. UE 637-000; 9% VA; MI=3.2 g/10 min.; (L) Ultrathene™ resin No. UE 656-003; 12.5% VA; MI=5.5 g/10 min.; (M) Ultrathene™ resin No. UE 631-000; 19% VA; MI=2.3 g/10 min.; and (N) Ultrathene™ resin No. UE 645-04; 28% VA; MI=3 g/10 min.

These EVA and EBA polymer resins were extruded into tubing using a 2.5 cm barrel Killion™ extruder and a single layer die with a 0.6 cm centerpin, and a 0.5 cm bushing in the sizing vacuum tank of the extrusion line. Extruder conditions for the single-layer extruded tubings of Comparative Examples G–N are shown in Table 9. Percent n-BA and VA and layer thickness in microns (µ) for the tubings of Comparative Examples G–N are shown in Table 10.

Comments Regarding Examples 19–26

Single-layer tubes formed from EBA copolymer, and EVA copolymer with a n-BA and VA content of 19% or less, respectively, were stiff, kinked easily, and were frequently cloudy or milky in appearance. In contrast, the EVA copolymer tubings with a VA content of 28% were flexible and kink resistant, but were also tacky to the touch, and easily scratched. Each of the single-layer tubing constructions were evaluated for incorporation into the multilayered tubings of the Examples of the present application.

EXAMPLES 27–35

Two Layer Tubing of all EVA or EVA/EBA

A series of two-layered tubing constructions was made from combinations of EVA of varying percent VA contents, and from a combination of an EVA copolymer (28% by weight VA) and an EBA copolymer of varying percent n-BA contents. All of the EVA and EBA resins used in these Examples of tubing constructions were obtained from Quantum Chemical Company, Rolling Meadows, Ill. Specific Quantum Chemical Co. EVA and EBA resins employed, included: (1) Enathene™ resin No. EA 705-009; 5% n-butyl acrylate (n-BA); MI=3 g/10 min.; (2) Enathene™ resin No. EA 719-009; 19% n-BA; MI=0.3 g/10 min.; (3) Petrothene™ resin No. NA 420; 2.5% VA; MI=2.5 g/10 min.; (4) Petrothene™ resin No. NA 316-138; 6% VA; MI=1.3 g/10 min.; (5) Ultrathene™ resin No. UE 637-000; 9% VA; MI=3.2 g/10 min.; (6) Ultrathene™ resin No. UE 651-109; 12.5% VA; MI=0.45 g/10 min.; (7) Ultrathene™ resin No. UE 631-000; 19% VA; MI=2.3 g/10 min.; and (8) Ultrathene™ resin No. UE 645-04; 28% VA; MI=3 g/10 min.

These resins were coextruded into the varying tubing constructions of Examples 27–35 by using the same extruders, multilayer die, center pin, and bushing as used in Examples 19–22. Specific extruder conditions for the two-layered EVA/EVA coextruded tubings of Examples 27–33 are shown in Table 11, and for the two-layered EVA/EBA coextruded tubings of Examples 34–35 in Table 12. Average thicknesses in microns (μ) for the inner layer, outside surface and the total layers of the Example 27–35 tubings were determined as in Examples 19–22, and are shown in Table 13.

The multilayered tubings of Examples 27–35 demonstrate that the addition of a thin outside surface of an EVA or EBA copolymer with a VA or n-BA content of 19% or less, respectively, to an inner layer of EVA with a VA content of 28%, provides a tubing which is tough, scratch-resistant, and flexible, and yet is environmentally compatible.

EXAMPLES 36–41

Three-Layer Tubing of all EVA or EVA/EBA

Six, three-layered coextruded tubing constructions, of the same form as illustrated in FIG. 2 herein, were made from combinations of EVA copolymers of varying percent VA contents, and from a combination of an EVA copolymer (28% VA) and an EBA copolymer (19% n-BA). All of the EVA and EBA resins used in three Examples of tubing constructions were obtained from Quantum Chemical Co., Rolling Meadows, Ill. Specific Quantum Chemical Co. EVA and EBA resins, included: (1) Enathene™ resin No. EA 719-009; 19% n-BA; MI 0.3 g/10 min.); (2) Petrothene™ resin No. NA 316-138; 6% VA; MI 1.3 g/10 min.; (3) Ultrathene™ resin No. UE 637-000; 9% VA; MI=3.2 g/10 min.; (4) Ultrathene™ resin No. UE 631-000; 19% VA; MI=2.3 g/10 min.; (5) Ultrathene™ resin No. UE 645-04; 28% VA; MI=3 g/10 min.

These resins were coextruded into the three-layered tubing constructions of Examples 36–41 using a single 2.5 cm barrel Killion™ extruder for the middle layer, and two 1.3 cm barrel Randcastle Microtruder™ extruders for the inner and outside surfaces. The three extruders were secured to a multilayered die with a 0.6 cm center pin, and a 0.5 cm bushing was used in the sizing vacuum tank of the extrusion line. Specific extruder conditions for the EVA/EVA/EVA and EBA/EVA/EBA coextruded tubing are shown in Table 14. Average thicknesses (μ) for the inner layer, middle layer, outside surface and total tube layers are shown in Table 15.

The multilayered tubings of Examples 36–41 demonstrate that the addition of a thin outside surface and a thin inner layer of an EVA or EBA copolymer with a VA or n-BA content of 19% or less, respectively, to an inner EVA layer with a VA content of 28% yields a preferred structure according to the present invention. In particular, such structures provide a tough, scratch-resistant tubing which maintains the flexibility of the 28% VA content EVA core, protected by the durable inner and outside surfaces, and is environmentally compatible due to a lack of chlorine-containing materials therein.

EXAMPLES 42–44

ABA Three-Layer Tubings

Three ABA three-layered tubings composed of an inner layer (B) and outside and inside surface layers (A) were coextruded from a multilayer tubing die as described in Example 1 with the specific conditions given in Table 1.

The A layers of each of the tubings of Examples 42–44 were composed of an ethylene/methacrylic acid copolymer zinc doped ionomer resin (EMAZ) commercially available as "Surlyn™ resin No. 1652" from E. I. DuPont de Nemours and Company, Wilmington, Del.

The B layer of each of the tubings of Examples 42–44 was comprised of an EVA copolymer with a 28% by weight VA content commercially available as "Ultrathene™ resin No. UE 645-04"; Melt Index(MI)=3 g/10 min; density=0.95 g/cc; from Quantum Chemical Corp., Rolling Meadows, Ill.

Outside diameter, inside diameter, load at 50% strain, stress at 50% strain, and Young's modulus were determined by using the test methods described above. The results are shown in Table 16. "Surlyn™ 1652" resin has a relatively high modulus, thus increasing the level of "Surlyn™ 1652" resin increases the tensile strength and the Young's modulus of the tubing. The tubings in these examples were comparable to plasticized PVC in tensile strength, but with a higher Young's modulus and stiffness.

COMPARATIVE EXAMPLE O

A single layer tubing was extruded as described in Comparative Example F and Table 3. The composition of the tubing was an ethylene/methacrylic acid (EMAA) zinc doped ionomer resin commercially available as "Surlyn™ resin No. 1652" from E. I. Du Pont de Nemours and Company, Wilmington, Del.

Outside diameter, inside diameter, load at 50% strain, stress at 50% strain, and Young's modulus were determined by using the test methods described above. The results are shown in Table 16.

EXAMPLES 45–47

ABA Three-Layer Tubings

Three ABA three-layered tubings composed of an inner layer (B) and outside and inside surface layers (A) were coextruded from a multilayer tubing die as described in Example 1 with the specific conditions given in Table 1.

The A layers of each of the tubings of Examples 45–47 were comprised of a ethylene/methacrylic acid copolymer zinc doped ionomer resin (EMAZ) commercially available as "Surlyn™ resin No. AD 8255"; Melt Index(MI)=4 g/10 min; from E. I. DuPont de Nemours and Company, Wilmington, Del.

The B layer of each of the tubings of Examples 45–47 was composed of an EVA copolymer with a 28% by weight VA content commercially available as "Ultrathene™ resin No. UE 645-04"; MI=3 g/10 min; density=0–95 g/cc; from Quantum Chemical Corp., Rolling Meadows, Ill.

Inside, inner, and outside layer thickness, relative layer thickness, outside diameter, inside diameter, load at 50% strain, stress at 50% strain, Young's modulus, recovery from 50% strain, and kink/re-kink resistance were determined by using the test methods described above. The results are shown in Table 16.

EXAMPLE 48

ABA Three-Layer Tubing

One ABA three-layered tubing composed of an inner layer (B) and outside and inside surface layers (A) were coextruded from a multilayer tubing die as described in Example 1 with the specific conditions given in Table 1.

The A layers of the tubing of Example 48 were composed of an ethylene/methacrylic acid (EMAS) sodium doped ionomer resin commercially available as "Surlyn™ resin No. 1601B" from E. I. Du Pont de Nemours and Company, Wilmington, Del.

The B layer of the tubing of Example 48 was comprised of an EVA copolymer with a 28% by weight VA content commercially available as "Ultrathene™ resin No. UE 645-04"; MI=3 g/10 min; density=0–95 g/cc; from Quantum Chemical Corp., Rolling Meadows, Ill.

Outside diameter, inside diameter, load at 50% strain, stress at 50% strain, and Young°s modulus were determined by using the test methods described above. The results are shown in Table 17. The tubing was clear and free of obvious layer incompatibility. It was very stiff and very strong.

COMPARATIVE EXAMPLES P–S

Single layer tubings were extruded as described in Comparative Example F and Table 1 or 3. The composition of the tubing in Comparative Example P was an ethylene/methacrylic acid (EMAS) sodium doped ionomer resin commercially available as "Surlyn™ resin No. 1601B" from E. I. Du Pont de Nemours and Company, Wilmington, Del. The tubing in Comparative Example Q was an ethylene/methacrylic acid (EMAZ) zinc doped ionomer resin commercially available as "Surlyn™ resin No. 9020" from E. I. Du Pont de Nemours and Company, Wilmington, Del. The tubing of Comparative Example R was composed of an ethylene/butene copolymer (EB) commercially available as "Exact™ resin No. 4024"; MI=3.8 dg/min; density=0.885 g/cc; from Exxon Chemical Company, Houston, Tex. The tubing of Comparative Example S was composed of a styrene butadiene block copolymer commercially available as "Kraton™ resin No. K2701" from Shell Oil Co., Houston, Tex.

Outside diameter, inside diameter, load at 50% strain, stress at 50% strain, and Young's modulus were determined by using the test methods described above. The results are shown in Table 17.

EXAMPLE 49

ABA Three-Layered Tubing

One ABA three-layered tubing composed of an inner layer (B) and outside and inside surface layers (A) were coextruded from a multilayer tubing die as described in Example 1 with the specific conditions given in Table 1.

The A layers of the tubing of Example 49 were composed of an ethylene/methacrylic acid (EMAZ) zinc doped ionomer resin commercially available as "Surlyn™ resin No. 9020" from E. I. Du Pont de Nemours and Company, Wilmington, Del.

The B layer of the tubing of Example 49 was comprised of an EVA copolymer with a 28% by weight VA content commercially available as "Ultrathene™ resin No. UE 645-04"; MI=3 g/10 min; density=0.95 g/cc; from Quantum Chemical Corp., Rolling Meadows, Ill.

Outside diameter, inside diameter, load at 50% strain, stress at 50% strain, and Young's modulus were determined by using the test methods described above. The results are shown in Table 17. The tubing was clear and free of obvious layer incompatibility. The Young's modulus was higher that those in Examples 1–12.

EXAMPLE 50

EMAZ Three-Layered Tubing

One ABA three-layered tubing composed of an inner layer (B) and outside and inside surface layers (A) was coextruded from a multilayer tubing die as described in Example 1 with the specific conditions given in Table 1.

The A layers of the tubing of Example 50 were comprised of an ethylene/methacrylic acid (EMAZ) zinc doped ionomer resin commercially available as "Surlyn™ resin No. 1652" from E. I. Du Pont de Nemours and Company, Wilmington, Del.

The B layer of the tubing of Example 50 was comprised of an ethylene/butene copolymer (EB) commercially available as "Exact™ resin No. 4024"; MI=3.8 dg/min; density= 0.885 g/cc; from Exxon Chemical Company, Houston, Tex.

Outside diameter, inside diameter, load at 50% strain, stress at 50% strain, and Young's modulus were determined by using the test methods described above. The results are shown in Table 17. The tubing was clear and free of obvious layer incompatibility. The Young's modulus was higher that those in Examples 1–12.

EXAMPLE 51

Styrene Block Three-Layered Tubing

One ABA three-layered tubing composed of an inner layer (B) and outside and inside surface layers (A) was coextruded from a multilayer tubing die as described in Example 1 with the specific conditions given in Table 1.

The A layers of the tubing of Example 51 were comprised of an ethylene/methacrylic acid (EMAZ) zinc doped ionomer resin commercially available as "Surlyn™ resin No. 1652" from E. I. Du Pont de Nemours and Company, Wilmington, Del.

The B layer of the tubing of Example 51 was comprised a styrene butadiene block copolymer of "Kraton™ resin No. K2701" from Shell Oil Co., Houston, Tex.

Outside diameter, inside diameter, load at 50% strain, stress at 50% strain, and Young's modulus were determined by using the test methods described above. The results are shown in Table 17. The tubing was clear and free of obvious layer incompatibility. The Young's modulus was higher that those in Examples 1–12.

EXAMPLE 52

EVA Three-Layered Tubing

One ABA three-layered tubing composed of an inner layer (B) and outside and inside surface layers (A) was coextruded using a 2.5 cm (1 inch) barrel Killion extruder and a 1.3 (½ inch) barrel Randcastle microtruder which were secured to a multilayer die with a 0.56 cm center pin. A 0.46 cm bushing was used in the sizing vacuum tank. Specific extruder conditions are shown in Table 18.

The A layers of the tubing of Example 52 were comprised of an ethylene/methacrylic acid (EMAZ) zinc doped ionomer resin commercially available as Surlyn™ resin No. 1702"; MI=14 g/10 min; density=0.941 g/cc; from E. I. Du Pont de Nemours and Company, Wilmington, Del.

The B layer was comprised of a blend of 80% EVA copolymer with a 28% by weight VA content commercially available as "Ultrathene™ resin No. UE 645-04"; MI=3 g/10 min; density=0.95 g/cc; from Quantum Chemical Corp., Rolling Meadows, Ill. and 20% EVA copolymer with a 31% by weight VA content commercially available as "Ultrathene™ resin No. UE 638-35"; MI=24 g/10 min; density=0.95 g/cc; from Quantum Chemical Corp., Rolling Meadows, Ill. The lower molecular weight "Ultrathene™ resin No. UE 638-35" was used to further soften the inner layer.

Average thicknesses (μ) for the inside layer (A), inner layer (B), outside layer (A), total tubing layers and kink/rekink resistance are shown in Table 21.

EXAMPLES 53–55

EMAA Three-Layered Tubing

Three ABA three-layered tubing composed of an inner layer (B) and outside and inside surface layers (A) were coextruded using a 2.5 cm (1 inch) barrel Killion extruder and a 1.3 (½ inch) barrel Randcastle microtruder which were secured to a multilayer die with a 0.56 cm center pin. A 0.46 cm bushing was used in the sizing vacuum tank. Specific extruder conditions are shown in Table 18.

The A layers of the tubings of Example 53–55 were comprised of an ethylene/methacrylic acid copolymer (EMAA) resin commercially available as "Nucrel™ resin No. 960"; MI=60 dg/min; density=0.941 g/cc; from E. I. Du Pont de Nemours and Company, Wilmington, Del.

The B layer was comprised of a blend of 80% EVA copolymer with a 28% by weight VA content commercially available as "Ultrathene™ resin No. UE 645-04"; MI=3 g/10 min; density=0.95 g/cc; from Quantum Chemical Corp., Rolling Meadows, Ill. and 20% EVA copolymer with a 31% by weight VA content commercially available as "Ultrathene™ resin No. UE 638-35"; MI=24 g/10 min; density=0.95 g/cc; from Quantum Chemical Corp., Rolling Meadows, Ill. The lower molecular weight "Ultrathene™ resin No. UE 638-35" was used to further soften the inner layer.

For Example 55, average thicknesses (μ) for the inside layer (A), inner layer (B), outside layer (A) total tubing layers and kink/rekink resistance are shown in Table 21.

EXAMPLES 56–58

EMAA Three-Layered Tubing

Three ABC three-layered tubing composed of an inner layer (B), outside layer (A) and inside layer (C) were coextruded using a 2.5 cm (1 inch) barrel Killion extruder, a 1.3 (½ inch) barrel Randcastle microtruder, and a 1.9 cm barrel Wayne extruder which were secured to a multilayer die with a 0.56 cm center pin. A 0.46 cm bushing was used in the sizing vacuum tank. Specific extruder conditions are shown in Table 19.

The A layer of the tubings of Example 56–58 was comprised of an ethylene/methacrylic acid copolymer (EMAA) resin commercially available as "Nucrel™ resin No. 960"; MI=60 dg/min; density=0.941 g/cc; from E. I. Du Pont de Nemours and Company, Wilmington, Del.

The B layer was comprised of a blend of 80% EVA copolymer with a 28% by weight VA content commercially available as "Ultrathene™ resin No. UE 645-04"; MI=3 g/10 min; density=0.95 g/cc; from Quantum Chemical Corp., Rolling Meadows, Ill. and 20% EVA copolymer with a 31% by weight VA content commercially available as "Ultrathene™ resin No. UE 638-35"; MI=24 g/10 min; density=0.95 g/cc; from Quantum Chemical Corp., Rolling Meadows, Ill. The lower molecular weight "Ultrathene™ resin No. UE 638-35" was used to further soften the inner layer.

The C layer was comprised of either an ethylene/vinyl acetate copolymer (EVA) with a 6% by weight VA content commercially available as "Petrothene™ resin No. NA 316-138"; MI=1.3 g/10 min; from Quantum Chemical Corp., Rolling Meadows, Ill. or an ethylene/vinyl acetate copolymer (EVA) with a 12.5% by weight VA content commercially available as "Ultrathene™ resin No. UE 651-109"; MI=0.45 g/10 min; from Quantum Chemical Corp., Rolling Meadows, Ill.

EXAMPLES 59–68

EMAA Three-Layered Tubing

Ten ABC three-layered tubing composed of an inner layer (B), outside surface layer (A) and inside surface layer (C) were coextruded using a 2.5 cm (1 inch) barrel Killion extruder, a 1.3 (½ inch) barrel Randcastle microtruder, and a 1.9 cm barrel Wayne extruder which were secured to a multilayer die with a 0.56 cm center pin. A 0.46 cm bushing was used in the sizing vacuum tank. Specific extruder conditions are shown in Table 20.

The A layer of the tubings of Examples 59–68 was comprised of an ethylene/methacrylic acid copolymer (EMAA) resin commercially available as "Nucrel™ resin No. 960"; MI=60 dg/min; density=0.941 g/cc; from E. I. Du Pont de Nemours and Company, Wilmington, Del.

The B layer was comprised of a blend of 80% EVA copolymer with a 28% by weight VA content commercially available as "Ultrathene™ resin No. UE 645-04"; MI=3 g/10 min; density=0.95 g/cc; from Quantum Chemical Corp., Rolling Meadows, Ill. and 20% EVA copolymer with a 31% by weight VA content commercially available as "Ultrathene™ resin No. UE 638-35"; MI=24 g/10 min; density=0.95 g/cc; from Quantum Chemical Corp., Rolling Meadows, Ill. The lower molecular weight "Ultrathene™ resin No. UE 638-35" was used to further soften the inner layer.

The C layer was comprised of an ethylene/methacrylic acid (EMAZ) zinc doped ionomer resin commercially available as "Surlyn™ resin No. 1702"; MI=14 g/10 min; density=0.941 g/cc; from E. I. Du Pont de Nemours and Company, Wilmington, Del.

Average thicknesses (μ) for the inside layer (A), inner layer (B), outside layer (A), total tubing layers and kink/rekink resistance are shown in Table 21.

EXAMPLE 69

ABC Three-Layered Tubing

One ABC three-layered tubing composed of an inner layer (B), outside surface layer (A) and inside surface layer (C) was coextruded using a 2.5 cm (1 inch) barrel Killion extruder, a 1.3 (½ inch) barrel Randcastle microtruder, and a 1.9 cm barrel Wayne extruder which were secured to a multilayer die with a 0.56 cm center pin. A 0.46 cm bushing was used in the sizing vacuum tank. Specific extruder conditions are shown in Table 20.

The A layer of the tubing of Example 69 was comprised of an ethylene/methacrylic acid copolymer (EMAZ) zinc doped ionomer resin commercially available as "Surlyn™ resin No. 1702"; MI=14 g/10 min; density=0.941 g/cc; from E. I. Du Pont de Nemours and Company., Wilmington, Del.

The B layer was comprised of a blend of 80% EVA copolymer with a 28% by weight VA content commercially available as "Ultrathene™ resin No. UE 645-04"; MI=3 g/10 min; density=0.95 g/cc; from Quantum Chemical Corp., Rolling Meadows, Ill. and 20% EVA copolymer with a 31% by weight VA content commercially available as "Ultrathene™ resin No. UE 638-35"; MI=24 g/10 min; density=0.95 g/cc; from Quantum Chemical Corp., Rolling Meadows, Ill. The lower molecular weight "Ultrathene™ resin No. UE 638-35" was used to further soften the inner layer.

The C layer was comprised of an ethylene/methacrylic acid (EMAA) resin commercially available as "Nucrel™ resin No. 960"; MI=60 dg/min; density=0.941 g/cc; from E. I. Du Pont de Nemours and Company, Wilmington, Del.

EXAMPLE 70

Tubing Clamp Test

Tubing of Example 11 was connected to an IV bag. Water was allowed to flow through the tubing to remove any air. The lumen of the tubing was clamped off with a pinch clamp until the water flow stopped. The bag was filled with 1000 ml of water and allowed to stand for two minutes. The clamp was released, and the time required to drain the 1000 ml of water was recorded. Water was allowed to flow through the tubing to remove air again. The lumen was clamped off for 45 hours and the bag refilled with 1000 ml of water. The clamp was released and the flow began again immediately. The time required to drain the bag originally was 292 seconds. The time required to drain the bag after 45 hours was 270 seconds. The tubing wall from Example 11 had sufficient resilience to recover completely from being clamped for 45 hours.

EXAMPLE 71

Extraction

Extraction studies were done on ABA multilayered tubing samples made like those described in Example 10 using "Surlyn™ resin No. 9320" which is a zinc doped ionomer resin for the inside and outside layers; in Example 7 using "Surlyn™ resin No. 8320" which is a sodium doped ionomer resin for the inside and outside layers; and in Example 18 using "Surlyn™ resin No. AD 8255" which is a zinc doped ionomer resin. The inner layer in each, Example 10, 7, and 18; was "Exact™ resin No. 4028".

A 203.2 cm (80 inch) length of each type of tubing was cut into 5.08 cm (2 inch) sections and placed in 50 ml bottles with foil lined caps. 20 ml of extraction fluids such as medical grade saline, dextrose, or a fat emulsion were added to each bottle containing the tubing samples and to bottles without tubing. The bottles were tumbled on a 2 rpm rotator for 4 days.

The extraction fluids were analyzed for levels of zinc or sodium. Control extraction fluids without tubing were analyzed for levels of zinc and sodium. The results are shown in Table 22.

In addition, the dextrose extraction fluid was analyzed for trace organics. Organic fragments with some carbonyl and some unsaturation were found in the part per billion range.

TABLE 1

Extruder conditions for three layer-tubings of Examples 1–12 (INNER = inner layer; I/O = inside and outside layers) and for single-layer tubings of Comparative Examples B–E.

| | Example Nos. | | | |
|---|---|---|---|---|
| | 1–12 | | Comp. Ex. B–D | Comp Ex. E |
| LAYER: | INNER | I/O | SINGLE | SINGLE |
| BARREL (cm): | 2.5 | 1.3 | 1.3 | 1.3 |
| Zone 1 temp (°C.) | 121 | 135 | 135 | 121 |
| Zone 2 temp (°C.) | 157 | 163 | 163 | 154 |
| Zone 3 temp (°C.) | 177 | 177 | 177 | 177 |
| Zone 4 CLP temp (°C.) | 179 | 177 | 177 | 177 |
| Melt Tube temp (°C.) | | | | |
| Die Temp (°C.) | 182 | 182 | 182 | 179 |
| RPM | 5 | 5–30 | 25 | 20 |
| Melt Temp (°C.) | | | | |
| Pressure (MPa) | | | | 8.3 |
| Amps | | | | 2 |
| Internal Air Pressure (cm H$_2$O) | | | | |
| VACUUM TANK: | | | | |
| Water Temp (°C.) | 13 | 13 | 13 | 21 |
| PULLER: | | | | |
| Speed (cm/min) | 152 | 152 | 152 | 2804 |

TABLE 2

Inside, inner, and outside layer thickness, relative layer thickness, dimensions, physical properties, kink/rekink resistance for three-layered (ABA) tubings of Examples 1–12 and dimensions, physical properties, and kink/rekink resistance for Comparative Examples A–E.

| Example | Layer Thickness A = Inside  B = Inner  A = Outside (cm) | | | Relative Layer Thickness A/B/A | OD/ID (cm) | Load at 50% Strain (kgf) | Strain at 50% Strain (MPa) | Young's Modulus (MPa) | Recovery From 50% Strain (%) | Kink/Rekink |
|---|---|---|---|---|---|---|---|---|---|---|
| Comp. A (PVC) | | | | | 0.412/0.310 | 3.95 | 6.8 | 20.4 | 96 | 2.5/2.1 |
| Examples 1–3 A/B/A = Surlyn ™ 8320/EVA/Surlyn ™ 8320 | | | | | | | | | | |
| Comp. B | | | | 0/100/0 | | | | 18.6 | | 1.6/<1.2 |
| 1 | 0.01161 | 0.05390 | 0.01003 | 15/71/13 | 0.409/0.259 | 2.75 | 3.4 | 20.9 | | |
| 2 | 0.01303 | 0.04458 | 0.01097 | 19/65/16 | 0.409/0.271 | 2.91 | 3.9 | 25.0 | 91 | 2.7/2.5 |
| 3 | 0.01575 | 0.04420 | 0.01499 | 21/59/20 | 0.424/0.274 | 3.09 | 3.7 | 21.7 | 90 | 2.8/2.7 |
| Comp. C | | | | 100/0/0 | 0.401/0.297 | 2.65 | 4.6 | 25.5 | | 2.6/2.1 |
| Examples 4–6 A/B/A = Surlyn ™ 9320/EVA/Surlyn ™ 9320 | | | | | | | | | | |
| 4 | 0.01265 | 0.04806 | 0.01041 | 18/68/15 | 0.394/0.254 | 2.75 | 3.8 | 23.1 | | |
| 5 | 0.01626 | 0.04724 | 0.01394 | 21/61/18 | 0.417/0.262 | 3.26 | 3.9 | 23.8 | 93 | 2.8/2.6 |
| 6 | 0.01852 | 0.03292 | 0.01646 | 27/48/24 | 0.412/0.274 | 3.12 | 4.1 | 25.6 | 94 | 2.6/2.4 |
| Comp. D | | | | 100/0/0 | 0.384/0.297 | 2.24 | 4.8 | 26.1 | | 2.6/2.1 |
| Examples 7–9 A/B/A = Surlyn ™ 8320/Exact ™ 4028/Surlyn ™ 8320 | | | | | | | | | | |
| Comp. E | | | | 0/100/0 | 0.412/0.279 | 2.17 | 3.0 | 17.0 | | 2.3/1.3 |
| 7 | 0.01257 | 0.04681 | 0.01048 | 18/67/15 | 0.404/0.264 | 2.57 | 3.4 | 20.6 | 93 | 3.2/3.1 |
| 8 | 0.01816 | 0.05118 | 0.01321 | 22/62/16 | 0.409/0.244 | 2.71 | 3.1 | 19.2 | 91 | 3.1/3.0 |
| 9 | 0.02098 | 0.03673 | 0.01725 | 28/49/23 | 0.414/0.264 | 2.89 | 3.6 | 21.5 | 90 | 3.0/2.8 |
| Examples 10–12 A/B/A = Surlyn ™ 9320/Exact ™ 4028/Surlyn ™ 9320 | | | | | | | | | | |
| 10 | 0.01354 | 0.04806 | 0.01151 | 19/66/16 | 0.401/0.297 | 2.84 | 3.8 | 23.4 | 93 | 2.9/2.6 |
| 11 | 0.01798 | 0.03973 | 0.01725 | 24/53/23 | 0.401/0.251 | 2.97 | 3.8 | 22.8 | 94 | 2.7/2.5 |
| 12 | 0.02096 | 0.03073 | 0.01816 | 30/44/26 | 0.389/0.249 | 2.84 | 4.0 | 23.8 | 94 | 2.6/2.3 |

TABLE 3

Extruder conditions for three layer-tubings of Examples 13–17 (INNER = inner layer; I/O = inside and outside layers) and for single-layer tubing of Comparative Example F and R.

| | Example No. | | | |
|---|---|---|---|---|
| | 13–17 | | Comp. Ex. F | Comp Ex. R |
| LAYER: | INNER | I/O | SINGLE | SINGLE |
| BARREL (cm): | 2.5 | 1.3 | 1.3 | 1.3 |
| Zone 1 temp (°C.) | 163 | 141 | 154 | 121 |
| Zone 2 temp (°C.) | 166 | 174 | 177 | 177 |
| Zone 3 temp (°C.) | 182 | 182 | 196 | 204 |
| Zone 4 CLP temp (°C.) | 193 | 188 | 221 | 216 |
| Melt Tube temp (°C.) | | | | |
| Die Temp (°C.) | 191 | 191 | 207 | 216 |
| RPM | 26.8 | 56.5 | | |
| Melt Temp (°C.) | 182 | 156 | | |
| Pressure (MPa) | 13.3 | 14.1 | 3.4 | 7 |
| Amps | 1.8 | 4–4.5 | 2 | 2 |
| Internal Air Pressure (cm H$_2$O) | | | | |
| VACUUM TANK: | | | | |
| Water Temp (°C.) | 21 | 21 | 21 | 21 |
| PULLER: | | | | |
| Speed (cm/min) | 594 | 594 | 305 | 5791 |

TABLE 4

Inside, inner, and outside layer thickness, relative layer thickness, dimensions, physical properties, kink/rekink resistance for three-layered (ABA) tubings of Examples 13–18 and dimensions, physical properties, and kink/rekink resistance for Comparative Examples A, E–F.

| Example | Layer Thickness A = Inside B = Inner A = Outside (cm) | | | Relative Layer Thickness A/B/A | OD/ID (cm) | Load at 50% Strain (kgf) | Stress at 50% Strain (MPa) | Young's Modulus Predicted/Measured (MPa) | Kink/Re-kink |
|---|---|---|---|---|---|---|---|---|---|
| Comp. A (PVC) | | | | | 0.412/0.310 | 3.95 | 6.8 | /20.4 | 2.5/2.1 |
| Examples 10–15 A/B/A = Surlyn ™ AD 8255/Exact ™ 4028/Surlyn ™ 8255 | | | | | | | | | |
| Comp. E | | | | 0/100/0 | 0.404/0.274 | 2.31 | | /14.4 | 2.4/1.4 |
| 13 | 0.00914 | 0.04775 | 0.00813 | 14/75/11 | 0.358/0.221 | 2.54 | | 20.2/21.2 | 2.8/2.0 |
| 14 | 0.01041 | 0.04343 | 0.00889 | 16/71/13 | 0.386/0.257 | 2.72 | | 21.2/18.8 | 2.7/2.2 |
| 15 | 0.01092 | 0.04039 | 0.01016 | 19/67/15 | 0.412/0.284 | 2.86 | | 22.1/19.3 | 2.6/2.0 |
| 16 | 0.01676 | 0.04039 | 0.01575 | 25/56/19 | 0.411/0.264 | 3.54 | | 24.5/21.4 | |
| 17 | 0.01549 | 0.03378 | 0.01397 | 26/53/21 | 0.391/0.267 | 3.27 | | 25.2/23.0 | 2.7/2.1 |
| Comp Ex. F | | | | 100/0/0 | 0.422/0.292 | 5.40 | | /37.3 | 2.3/1.2 |
| 18 | 0.01270 | 0.04750 | 0.01092 | 18/67/15 | 0.396/0.259 | 3.08 | 4.28 | /21.3 | 2.7/2.2 |

TABLE 5

Extruder conditions for the two-layered tubings of Examples 19–22
(IN = inner layer; OUT = outside layer).

| | Example No. | | | | | | | |
|---|---|---|---|---|---|---|---|---|
| | 19 | | 20 | | 21 | | 22 | |
| LAYER: | IN | OUT | IN | OUT | IN | OUT | IN | OUT |
| MATERIAL: | EVA | EVA | EVA | EVA | EVA | EVA | EVA | EVA |
| % VA | 28 | 6 | 28 | 6 | 28 | 6 | 28 | 6 |
| EXTRUDER BARREL (cm): | 2.5 | 1.3 | 2.5 | 1.3 | 2.5 | 1.3 | 2.5 | 1.3 |
| Zone 1 temp (°C.) | 149 | 179 | 149 | 179 | 149 | 179 | 149 | 179 |
| Zone 2 temp (°C.) | 171 | 182 | 171 | 182 | 171 | 182 | 171 | 182 |
| Zone 3 temp (°C.) | 171 | 188 | 171 | 188 | 171 | 188 | 171 | 188 |
| Zone 4 CLP temp (°C.) | 171 | 193 | 171 | 193 | 171 | 193 | 171 | 193 |
| Melt Tube temp (°C.) | 171 | 204 | 171 | 204 | 171 | 204 | 171 | 204 |
| Die Temp (°C.) | 174 | 174 | 174 | 174 | 174 | 174 | 174 | 174 |
| RPM | 22 | 5 | 18 | 10 | 20 | 15 | 23 | 18 |
| Melt Temp (°C.) | 169 | 182 | 169 | 182 | 169 | 182 | 169 | 182 |
| Pressure (MPa) | 17 | 16 | 17 | 19 | 18 | 11 | 18 | 11 |
| Amps | 2.0 | 1.3 | 2.8 | 1.0 | 2.8 | 1.3 | 2.9 | 1.2 |
| Internal Air Pressure (cm H$_2$O) | 6 | 6 | 6 | 6 | 6 | 6 | 6 | 6 |
| VACUUM TANK: | | | | | | | | |
| Sizing Pres (cm H$_2$O) | 25 | 25 | 25 | 25 | 25 | 25 | 25 | 25 |
| Water Temp (°C.) | 27 | 27 | 27 | 27 | 27 | 27 | 27 | 27 |
| PULLER: | | | | | | | | |
| Speed (cm/min) | 265 | 265 | 265 | 265 | 265 | 265 | 290 | 290 |

TABLE 6

Average thickness for the inner layer, outside layer, and total average thickness in microns (μ) for the two-layered tubings of Examples 19–22.

| Example Number | Average Inner Layer Thickness (μ) | Average Ouside Layer Thickness (μ) | Total Average Layer Thicknesses (μ) |
|---|---|---|---|
| 19 | 825 | 40 | 865 |
| 20 | 845 | 50 | 895 |
| 21 | 780 | 85 | 865 |
| 22 | 838 | 67 | 905 |

TABLE 7

Extruder conditions for the two-layered tubings of Examples 23–26
(IN = inner layer; OUT = outside layer).

| | Example No. | | | | | | | |
|---|---|---|---|---|---|---|---|---|
| | 23 | | 24 | | 25 | | 26 | |
| LAYER: | IN | OUT | IN | OUT | IN | OUT | IN | OUT |
| MATERIAL: | EVA | EVA | EVA | EVA | EVA | EVA | EVA | EVA |
| % VA | 28 | 6 | 28 | 6 | 28 | 6 | 28 | 6 |
| EXTRUDER BARREL (cm): | 2.5 | 1.3 | 2.5 | 1.3 | 2.5 | 1.3 | 2.5 | 1.3 |
| Zone 1 temp (°C.) | 149 | 179 | 149 | 179 | 149 | 179 | 149 | 179 |
| Zone 2 temp (°C.) | 166 | 193 | 166 | 193 | 166 | 182 | 166 | 182 |
| Zone 3 temp (°C.) | 166 | 188 | 166 | 188 | 166 | 188 | 166 | 188 |
| Zone 4 CLP temp (°C.) | 166 | 193 | 166 | 193 | 166 | 193 | 166 | 193 |
| Melt Tube temp (°C.) | 166 | 163 | 166 | 163 | 166 | 163 | 166 | 163 |
| Die Temp (°C.) | 171 | 171 | 171 | 171 | 171 | 171 | 171 | 171 |
| RPM | 23 | 17 | 23 | 22 | 23 | 12 | 23 | 6 |
| Melt Temp (°C.) | 169 | 180 | 169 | 180 | 169 | 180 | 169 | 180 |
| Pressure (MPa) | 18 | 10 | 18 | 11 | 18 | 7 | 18 | 6 |
| Amps | 2.8 | 1.2 | 2.8 | 1.2 | 1.9 | 1.0 | 1.9 | 1.0 |
| Internal Air Pressure (cm H$_2$O) | 3 | 3 | 3 | 3 | 3 | 3 | 3 | 3 |
| VACUUM TANK: | | | | | | | | |
| Sizing Pres (cm H$_2$O) | 25 | 25 | 25 | 25 | 25 | 25 | 25 | 25 |
| Water Temp (°C.) | 21 | 21 | 21 | 21 | 18 | 18 | 18 | 18 |
| PULLER: | | | | | | | | |
| Speed (cm/min) | 259 | 259 | 259 | 259 | 259 | 259 | 259 | 259 |

TABLE 8

Average thicknesses for the inner layer, outside layer, and total average thickness in microns (μ) for the two-layered tubings of Examples 23–26.

| Example Number | Average Inner Layer Thickness (μ) | Average Outer Layer Thickness (μ) | Total Average Layer Thicknesses (μ) |
|---|---|---|---|
| 5 | 893 | 37 | 930 |
| 6 | 1063 | 76 | 1139 |
| 7 | 958 | 58 | 1016 |
| 8 | 943 | 58 | 1001 |

TABLE 9

Extruder conditions for single-layer tubings of Comparative Examples G–N.

| | Comparative Example No. | | | | | | | |
|---|---|---|---|---|---|---|---|---|
| | G | H | I | J | K | L | M | N |
| MATERIAL: | EBA | EBA | EVA | EVA | EVA | EVA | EVA | EVA |
| % VA–% n-BA | 5 | 19 | 2.5 | 6 | 9 | 12.5 | 19 | 28 |
| BARREL (cm): | 2.5 | 2.5 | 2.5 | 2.5 | 2.5 | 2.5 | 2.5 | 2.5 |
| Zone 1 temp (°C.) | 168 | 168 | 168 | 168 | 168 | 168 | 168 | 149 |
| Zone 2 temp (°C.) | 177 | 177 | 177 | 177 | 177 | 177 | 177 | 160 |
| Zone 3 temp (°C.) | 185 | 185 | 185 | 185 | 185 | 185 | 185 | 166 |
| Zone 4 temp (°C.) | 191 | 191 | 191 | 191 | 191 | 191 | 191 | 166 |
| Melt Tube temp (°C.) | 191 | 191 | 191 | 191 | 191 | 191 | 191 | 166 |
| Die Temp (°C.) | 193 | 193 | 193 | 193 | 196 | 193 | 193 | 171 |
| RPM | 20 | 16 | 19 | 17 | 17 | 17 | 16 | 16 |
| Melt Temp (°C.) | 188 | 187 | 188 | 187 | 188 | 187 | 187 | 166 |
| Pressure (MPa) | 12 | 21 | 13 | 16 | 12 | 20 | 17 | 0 |
| Amps | 1.2 | 2.0 | 2.0 | 1.6 | 1.8 | 2.0 | 1.6 | 2.2 |
| Internal Air Pressure (cm H$_2$O) | 5 | 5 | 5 | 5 | 5 | 5 | 5 | 0 |
| VACUUM TANK: | | | | | | | | |
| Sizing Pres (cm H$_2$O) | 20 | 20 | 20 | 20 | 20 | 20 | 20 | 20 |
| Water Temp (°C.) | 26 | 26 | 26 | 26 | 26 | 26 | 26 | 26 |
| PULLER: | | | | | | | | |
| Speed (cm/min) | 229 | 229 | 229 | 229 | 229 | 229 | 235 | 235 |

TABLE 10

Percent n-BA and VA, layer thickness for single-layer tubings of Comparative Examples G–N.

| Comparative Example Number | EBA Content (% n-BA) | EVA Content (% VA) | Layer Thickness (μ) |
|---|---|---|---|
| G | 5 | — | 635 |
| H | 19 | — | 572 |
| I | — | 2.5 | 635 |
| J | — | 6 | 584 |
| K | — | 9 | 559 |
| L | — | 12.5 | 572 |
| M | — | 19 | 572 |
| N | — | 28 | 597 |

TABLE 11

Extruder conditions for two-layered tubings of Examples 27–33 (IN = inner layer; OUT = outside layer).

| | Example No. | | | | | | | | | | | | | |
|---|---|---|---|---|---|---|---|---|---|---|---|---|---|---|
| | 27 | | 28 | | 29 | | 30 | | 31 | | 32 | | 33 | |
| LAYER: | IN | OUT | IN | OUT | IN | OUT | IN | OUT | IN | OUT | IN | OUT | IN | OUT |
| MATERIAL: | EVA | EVA | EVA | EVA | EVA | EVA | EVA | EVA | EVA | EVA | EVA | EVA | EVA | EVA |
| % VA | 28 | 2.5 | 28 | 6 | 28 | 9 | 28 | 12.5 | 28 | 19 | 19 | 6 | 19 | 6 |
| EXTRUDER BARREL (cm): | 2.5 | 1.3 | 2.5 | 1.3 | 2.5 | 1.3 | 2.5 | 1.3 | 2.5 | 1.3 | 2.5 | 1.3 | 2.5 | 1.3 |
| Zone 1 temp (°C.) | 149 | 179 | 149 | 179 | 149 | 179 | 149 | 179 | 149 | 179 | 160 | 179 | 160 | 179 |
| Zone 2 temp (°C.) | 163 | 182 | 163 | 182 | 163 | 182 | 163 | 182 | 163 | 182 | 168 | 182 | 168 | 182 |
| Zone 3 temp (°C.) | 166 | 188 | 166 | 188 | 166 | 188 | 166 | 188 | 166 | 188 | 171 | 188 | 171 | 188 |

TABLE 11-continued

Extruder conditions for two-layered tubings of Examples 27–33 (IN = inner layer; OUT = outside layer).

| | \multicolumn{14}{c|}{Example No.} | | | | | | | | | | | | | |
|---|---|---|---|---|---|---|---|---|---|---|---|---|---|---|
| | 27 | | 28 | | 29 | | 30 | | 31 | | 32 | | 33 | |
| LAYER: | IN | OUT | IN | OUT | IN | OUT | IN | OUT | IN | OUT | IN | OUT | IN | OUT |
| Zone 4 CLP temp (°C.) | 166 | 193 | 166 | 193 | 166 | 193 | 166 | 193 | 166 | 193 | 171 | 193 | 171 | 193 |
| Melt Tube temp (°C.) | 166 | 166 | 166 | 166 | 166 | 166 | 166 | 166 | 166 | 166 | 171 | 171 | 171 | 171 |
| Die Temp (°C.) | 171 | 171 | 171 | 171 | 171 | 171 | 171 | 171 | 171 | 171 | 177 | 177 | 177 | 177 |
| RPM | 20 | 10 | 17 | 12 | 17 | 12 | 18 | 5 | 16 | 13 | 17 | 13 | 15 | 25 |
| Melt Temp (°C.) | 166 | 179 | 166 | 179 | 166 | 179 | 166 | 179 | 166 | 179 | 171 | 179 | 171 | 171 |
| Pressure (MPa) | 20 | 14 | 19 | 12 | 19 | 11 | 19 | 11 | 18 | 16 | 18 | 12 | 17 | 16 |
| Amps | 2.8 | 3.0 | 2.4 | 1.0 | 2.3 | 3.2 | 2.8 | 1.0 | 2.3 | 3.0 | 2.0 | 1.0 | 1.9 | 1.0 |
| Internal Air Pressure (cm H$_2$O) | 0.0 | 0.0 | 0.0 | 0.0 | 0.0 | 0.0 | 0.0 | 0.0 | 0.3 | 0.3 | 0.8 | 0.8 | 0.8 | 0.8 |
| \multicolumn{15}{c|}{VACUUM TANK:} | | | | | | | | | | | | | | |
| Sizing Pres (cm H$_2$O) | 20 | 20 | 15 | 15 | 20 | 20 | 20 | 20 | 20 | 20 | 20 | 20 | 20 | 20 |
| Water Temp (°C.) | 26 | 26 | 26 | 26 | 26 | 26 | 26 | 26 | 26 | 26 | 26 | 26 | 26 | 26 |
| \multicolumn{15}{c|}{PULLER:} | | | | | | | | | | | | | | |
| Speed (cm/min) | 305 | 305 | 259 | 259 | 259 | 259 | 244 | 244 | 259 | 259 | 244 | 244 | 229 | 229 |

TABLE 12

Extruder conditions for the two-layered tubings of Examples 34–35 (IN = inner layer; OUT = outside layer).

| | Example No. | | | |
|---|---|---|---|---|
| | 34 | | 35 | |
| Layer: | IN | OUT | IN | OUT |
| MATERIAL: % VA | EVA 28 | | EVA 28 | |
| % n-BA | | EBA 5 | | EBA 19 |
| EXTRUDER BARREL (cm): | 2.5 | 1.3 | 2.5 | 1.3 |
| Zone 1 temp (°C.) | 149 | 179 | 149 | 179 |
| Zone 2 temp (°C.) | 163 | 182 | 163 | 182 |
| Zone 3 temp (°C.) | 166 | 188 | 166 | 188 |
| Zone 4 CLP temp (°C.) | 166 | 193 | 166 | 193 |
| Melt Tube temp (°C.) | 166 | 166 | 166 | 166 |
| Die Temp (°C.) | 171 | 171 | 171 | 171 |
| RPM | 16 | 12 | 16 | 12 |
| Melt Temp (°C.) | 166 | 179 | 166 | 179 |
| Pressure (MPa) | 18 | 12 | 19 | 25 |
| Amps | 2.3 | 2.3 | 2.3 | 4.1 |
| Internal Air Pressure (cm H$_2$O) | 0 | 0 | 0 | 0 |
| VACUUM TANK: | | | | |
| Sizing Pres (cm H$_2$O) | 20 | 20 | 20 | 20 |
| Water Temp (°C.) | 24 | 24 | 26 | 26 |
| PULLER: | | | | |
| Speed (cm/min) | 244 | 244 | 244 | 244 |

TABLE 13

Average thicknesses for the inner layer, outside layer, and total layers for the two-layered tubings of Examples 27–35

| Example Number | Inner Layer Thick (μ) | Outside Layer Thick (μ) | Total Layers Thick (μ) |
|---|---|---|---|
| 27 | 582 | 85 | 667 |
| 28 | 558 | 48 | 606 |
| 29 | 563 | 88 | 651 |
| 30 | 603 | 25 | 628 |
| 31 | 558 | 73 | 631 |
| 32 | 578 | 49 | 627 |
| 33 | 535 | 95 | 630 |
| 34 | 555 | 89 | 644 |
| 35 | 536 | 83 | 619 |

TABLE 14

Extruder conditons for the three-layered tubings of Examples 36–41 (INNER = inner layer; I/O = inside and outside layers).

| | Example No. | | | | | | | | | | | |
|---|---|---|---|---|---|---|---|---|---|---|---|---|
| | 36 | | 37 | | 38 | | 39 | | 40 | | 41 | |
| LAYER: | INNER | I/O | INNER | I/O | INNER | I/O | INNER | I/O | INNER | I/O | INNER | I/O |
| MATERIAL: | EVA | EBA | EVA | EVA | EVA | EVA | EVA | EVA | EVA | EVA | EVA | EVA |
| % VA - % N-BA | 28 | 19 | 28 | 9 | 28 | 9 | 28 | 6 | 19 | 6 | 19 | 6 |
| EXTRUDER BARREL (cm): | 2.5 | 1.3 | 2.5 | 1.3 | 2.5 | 1.3 | 2.5 | 1.3 | 2.5 | 1.3 | 2.5 | 1.3 |
| Zone 1 temp (°C.) | 149 | 179 | 149 | 179 | 149 | 179 | 149 | 179 | 149 | 179 | 149 | 179 |
| Zone 2 temp (°C.) | 160 | 182 | 160 | 182 | 160 | 182 | 160 | 182 | 160 | 182 | 160 | 182 |
| Zone 3 temp (°C.) | 166 | 188 | 166 | 188 | 166 | 188 | 166 | 188 | 166 | 188 | 166 | 188 |
| Zone 4 CLP temp (°C.) | 166 | 193 | 166 | 193 | 166 | 193 | 166 | 193 | 166 | 193 | 166 | 193 |
| Melt Tube temp (°C.) | 166 | 177 | 166 | 177 | 166 | 177 | 166 | 177 | 166 | 177 | 166 | 177 |
| Die Temp (°C.) | 171 | 171 | 171 | 171 | 171 | 171 | 171 | 171 | 171 | 171 | 171 | 171 |
| RPM | 10 | 13 | 12 | 13 | 24 | 13 | 15 | 13 | 15 | 12 | 15 | 18 |
| Melt Temp (°C.) | 169 | 179 | 167 | 179 | 168 | 179 | 169 | 179 | 167 | 179 | 167 | 179 |
| Pressure (MPa) | 14 | 22 | 14 | 12 | 19 | 11 | 16 | 12 | 17 | 13 | 16 | 12 |
| Amps | 1.2 | — | 1.4 | 2.3 | 2.8 | 3.0 | 2.3 | 1.0 | 2.0 | 1.0 | 2.0 | 1.0 |
| Internal Air Pressure (cm $H_2O$) | 0.0 | 0.0 | 0.0 | 0.0 | 0.0 | 0.0 | 0.0 | 0.0 | 0.0 | 0.0 | 0.0 | 0.0 |
| VACUUM TANK: | | | | | | | | | | | | |
| Sizing Pres (cm $H_2O$) | 20 | 20 | 20 | 20 | 20 | 20 | 20 | 20 | 20 | 20 | 20 | 20 |
| Water Temp (°C.) | 26 | 26 | 26 | 26 | 26 | 26 | 26 | 26 | 26 | 26 | 26 | 26 |
| PULLER: | | | | | | | | | | | | |
| Speed (cm/min) | 177 | 177 | 229 | 229 | 229 | 229 | 235 | 235 | 229 | 229 | 229 | 229 |

TABLE 15

Average thicknesses for the inside layer, inner layer, outside layer, and total tube layers for the three-layered tubings of Examples 36–41.

| Example Number | Inside Layer Thick (μ) | Inner Layer Thick (μ) | Outside Layer Thick (μ) | Total Layer Thick (μ) |
|---|---|---|---|---|
| 36 | 88 | 492 | 57 | 637 |
| 37 | 72 | 512 | 62 | 645 |
| 38 | 56 | 785 | 32 | 873 |
| 39 | 33 | 557 | 32 | 622 |
| 40 | 39 | 557 | 26 | 622 |
| 41 | 102 | 534 | 34 | 670 |

TABLE 16

Inside, inner, and outside layer thickness, relative layer thickness, dimensions, physical properties, kink/rekink resistance for three-layered (ABA) tubings of Examples 42–47 and dimensions, physical properties, and kink/rekink resistance for Comparative Examples A, B, F and G.

| | Layer Thickness | | | Relative Layer Thickness | OD/ | Load at 50% | Stress at 50% | Young's | Recovery | |
|---|---|---|---|---|---|---|---|---|---|---|
| Example | A = Inside | B = Inner (cm) | A = Outside | A/B/A (%) | ID (cm) | Strain (kgf) | Strain (MPa) | Modulus (MPa) | From 59% Strain (%) | Kink/Rekink |
| Comp. A (PVC) | | | | | 0.411/0.310 | 3.95 | 6.8 | 20.4 | | 2.5/2.1 |
| Examples 42–44 A/B/A = Surlyn ™ 1652/EVA/Surlyn ™ 1652 | | | | | | | | | | |
| Comp. B (EVA) | | | | | 0/100/0 | | | 18.6 | | 1.6/<1.2 |
| 42 | 0.0154 | 0.0266 | 0.0133 | 28/48/24 | 0.411/0.300 | 4.12 | 6.5 | 52.3 | | 2.0/1.7 |
| 43 | 0.0152 | 0.0316 | 0.0117 | 26/54/20 | 0.401/0.284 | 3.77 | 5.9 | 46.8 | | 2.1/<1.2 |

TABLE 16-continued

Inside, inner, and outside layer thickness, relative layer thickness, dimensions, physical properties, kink/rekink resistance for three-layered (ABA) tubings of Examples 42–47 and dimensions, physical properties, and kink/rekink resistance for Comparative Examples A, B, F and G.

| Example | Layer Thickness A = Inside | B = Inner (cm) | A = Outside | Relative Layer Thickness A/B/A (%) | OD/ID (cm) | Load at 50% Strain (kgf) | Stress at 50% Strain (MPa) | Young's Modulus (MPa) | Recovery From 59% Strain (%) | Kink/Rekink |
|---|---|---|---|---|---|---|---|---|---|---|
| 44 | 0.0144 | 0.0316 | 0.0094 | 26/57/17 | 0.411/0.300 | 3.56 | 5.6 | 47.0 | | 2.0/<1.2 |
| Comp Ex. G | | | | 100/0/0 | 0.358/0.267 | 3.57 | 7.9 | 74.9 | | 1.6/<1.2 |
| Examples 45–47 A/B/A = Surlyn ™ AD-8255/EVA/Surlyn ™ AD-8255 | | | | | | | | | | |
| 45 | 0.01369 | 0.03795 | 0.01058 | 22/61/17 | 0.404/0.279 | 3.05 | 4.5 | 33.5 | 96 | 2.4/1.9 |
| 46 | 0.01369 | 0.03424 | 0.01433 | 22/55/23 | 0.404/0.279 | 3.42 | 5.0 | 39.4 | 96 | 2.3/1.9 |
| 47 | 0.02159 | 0.02540 | 0.01715 | 34/40/27 | 0.409/0.282 | 3.59 | 5.1 | 38.3 | 96 | 2.3/2.0 |
| Comp Ex. F | | | | 100/0/0 | 0.300/0.191 | 2.66 | 6.2 | 45.0 | | |

TABLE 17

Relative layer thickness, dimensions, physical properties, kink/rekink resistance for three-layered (ABA) tubings of Examples 25–28 and dimensions, physical properties, and kink/rekink resistance for Comparative Examples A, B, and O–S.

| Example | Relative Layer Thickness A/B/A (%) | OD/ID (cm) | Load at 50% Strain (kgf) | Stress at 50% Strain (MPa) | Young's Modulus (MPa) | Kink/Rekink |
|---|---|---|---|---|---|---|
| Comp. A (PVC) | | 0.411/0.310 | 3.95 | 6.8 | 20.4 | 2.5/2.1 |
| Example 48 A/B/A = Surlyn ™ 1601B/EVA/Surlyn ™ 1601B | | | | | | |
| Comp. B (EVA) | 0/100/0 | | | | 18.6 | 1.6/<1.2 |
| 48 | | 0.424/0.376 | 4.73 | 15.4 | 156.0 | |
| Comp. Ex. P | 100/0/0 | 0.318/0.216 | | 12.1 | 136.9 | |
| Example 49 A/B/A = Surlyn ™ 9020/EVA/Surlyn ™ 9020 | | | | | | |
| 49 | 15/70/15 | 0.414/0.325 | 2.83 | 5.4 | 46.5 | |
| Comp Ex. Q | 100/0/0 | | | | | |
| Example 50 A/B/A = Surlyn ™ 1652/Exact ™ 4024/Surlyn ™ 1652 | | | | | | |
| Comp Ex. R | 0/100/0 | | | | | |
| 50 | | 0.411/0.279 | 3.69 | | 44.1 | |
| Comp Ex. Q | 100/0/0 | 0.358/0.267 | 3.57 | 7.9 | 74.9 | |
| Example 51 A/B/A = Surlyn ™ 1652/Kraton ™ K2701/Surlyn ™ 1652 | | | | | | |
| Comp Ex. S | 0/100/0 | | | | | |
| 51 | | 0.411/0.279 | 4.84 | | 70.9 | |

TABLE 18

Extruder conditions for the three-layered tubings of Examples 52–55
(Inner = inner layer; I = inside layer; O = outside layer).

| | Example No. | | | | | | | |
|---|---|---|---|---|---|---|---|---|
| | 52 | | 53 | | 54 | | 55 | |
| LAYER: | INNER | I/O | INNER | I/O | INNER | I/O | INNER | I/O |
| MATERIAL: | EVA | EMAZ | EVA | EMAA | EVA | EMAA | EVA | EMAA |
| % VA | 28/31 | | 28/31 | | 28/31 | | 28/31 | |
| EXTRUDER BARREL (cm): | 2.5 | 1.3 | 2.5 | 1.3 | 2.5 | 1.3 | 2.5 | 1.3 |
| Zone 1 temp (°C.) | 172 | 168 | 172 | 168 | 172 | 168 | 172 | 168 |
| Zone 2 temp (°C.) | 177 | 169 | 177 | 169 | 177 | 169 | 177 | 169 |
| Zone 3 temp (°C.) | 177 | 174 | 177 | 174 | 177 | 174 | 177 | 174 |
| Zone 4 CLP temp (°C.) | 179 | 179 | 179 | 179 | 179 | 179 | 179 | 179 |
| Melt Tube temp (°C.) | 182 | 182 | 182 | 192 | 182 | 182 | 182 | 182 |
| Die Temp (°C.) | 182 | 182 | 182 | 182 | 182 | 182 | 182 | 182 |
| RPM | 14.4 | 6.6 | 19.4 | 13.2 | 14.0 | 8.0 | 14.0 | 6.6 |
| Melt Temp (°C.) | 181 | 166 | 181 | 166 | 179 | 166 | 181 | 166 |
| Pressure (MPa) | 8.3–8.8 | 2.7–2.8 | 12.6 | 1.5–2.1 | 9.0 | 1.7 | 8.3–8.8 | 1.4 |
| Amps | 1.9 | 2.1 | 2.0 | 0.5 | 2.0 | 1.5 | 1.9 | 1.2 |
| Internal Air Pressure (cm $H_2O$) | 3 | 3 | | | | | 3 | 3 |
| VACUUM TANK: | | | | | | | | |
| Sizing Pres (cm $H_2O$) | 20 | 20 | | | 20 | 20 | 20 | 20 |
| Water Temp (°C.) | 14 | 14 | | | | | 14 | 14 |
| PULLER: | | | | | | | | |
| Speed (cm/min) | 293 | 293 | 366 | 366 | 320 | 320 | 293 | 293 |

TABLE 19

Extruder conditions for the three-layered tubings of
Examples 56–58
(A = outside layer; B = inner layer; C = inside layer).

| | Example No. | | | | | | | | |
|---|---|---|---|---|---|---|---|---|---|
| | 56 | | | 57 | | | 58 | | |
| LAYER: | A | B | C | A | B | C | A | B | C |
| MATERIAL: | EMAA | EVA | EVA | EMAA | EVA | EVA | EMAA | EVA | EVA |
| % VA | | 28/31 | 12.5 | | 28/31 | 6 | | 28/31 | 6 |
| EXTRUDER BARREL (cm): | 1.3 | 2.5 | 1.9 | 1.3 | 2.5 | 1.9 | 1.3 | 2.5 | 1.9 |
| Zone 1 temp (°C.) | 168 | 172 | 168 | 168 | 172 | 168 | 168 | 172 | 168 |
| Zone 2 temp (°C.) | 181 | 177 | 177 | 181 | 177 | 177 | 181 | 177 | 177 |
| Zone 3 temp (°C.) | 174 | 177 | 179 | 174 | 177 | 179 | 174 | 177 | 179 |
| Zone 4 CLP temp (°C.) | 179 | 179 | 191 | 179 | 179 | 191 | 179 | 179 | 191 |
| Melt Tube temp (°C.) | 182 | 182 | 182 | 182 | 182 | 182 | 182 | 182 | 182 |
| Die Temp (°C.) | 182 | 182 | 182 | 182 | 182 | 182 | 182 | 182 | 182 |
| RPM | 4.5 | 17.5 | 3.0 | 4.5 | 20.1 | 3.0 | 4.5 | | 3.0 |
| Melt Temp (°C.) | 166 | 180 | NA | 166 | 180 | NA | 166 | 180 | NA |
| Pressure | 1.6 | 10.3 | NA | 1.6 | 11.7 | NA | 1.6 | | NA |

TABLE 19-continued

Extruder conditions for the three-layered tubings of
Examples 56–58
(A = outside layer; B = inner layer; C = inside layer).

| | \multicolumn{9}{c}{Example No.} | | | | | | | | |
|---|---|---|---|---|---|---|---|---|---|
| | | 56 | | | 57 | | | 58 | |
| LAYER: | A | B | C | A | B | C | A | B | C |
| (MPa) | | | | | | | | | |
| Amps | 1.5 | 2.0 | 2.5 | 1.5 | 2.3 | 2.5 | 1.5 | | 2.5 |
| | | | | PULLER: | | | | | |
| Speed (cm/min) | 366 | 366 | 366 | | | | | | |

TABLE 20

Extruder conditions for the three-layered tubings of
Examples 59–69
(A = outside layer; B = inner layer; C = inside layer).

| | \multicolumn{9}{c}{Example No.} | | | | | | | | |
|---|---|---|---|---|---|---|---|---|---|
| | | 59 | | | 60 | | | 61 | |
| LAYER: | A | B | C | A | B | C | A | B | C |
| MATERIAL: | EMAA | EVA | EMAZ | EMAA | EVA | EMAZ | EMAA | EVA | EMAZ |
| % VA | | 28/31 | | | 28/31 | | | 28/31 | |
| EXTRUDER BARREL (cm): | 1.3 | 2.5 | 1.9 | 1.3 | 2.5 | 1.9 | 1.3 | 2.5 | 1.9 |
| Zone 1 temp (°C.) | 168 | 172 | 168 | 168 | 172 | 168 | 168 | 172 | 168 |
| Zone 2 temp (°C.) | 182 | 177 | 177 | 182 | 177 | 177 | 182 | 177 | 177 |
| Zone 3 temp (°C.) | 174 | 177 | 179 | 174 | 177 | 179 | 174 | 177 | 179 |
| Zone 4 CLP temp (°C.) | 179 | 180 | 191 | 179 | 180 | 191 | 179 | 180 | 191 |
| Melt Tube temp (°C.) | 182 | 182 | 182 | 182 | 182 | 182 | 182 | 182 | 182 |
| Die Temp (°C.) | 182 | 182 | 182 | 182 | 182 | 182 | 182 | 182 | 182 |
| RPM | 3.6 | 11.8 | 4.0 | 4.6 | 16.4 | 3.5 | 9.7 | 15.8 | 4.5 |
| Melt Temp (°C.) | 166 | 198 | NA | 166 | 197 | NA | 166 | 197 | NA |
| Pressure (MPa) | 0.3 | 7.9–8.1 | NA | 0–0.1 | 9.7 | NA | 0.8 | 9.0–9.7 | NA |
| Amps | 1.0 | 1.8 | 2.0 | 1.2 | 2.0 | 2.0 | 1.5 | 1.8 | 2.1 |
| Internal Air Pressure (cm $H_2O$) | 1.3 | 1.3 | 1.3 | 10.9 | 10.9 | 10.9 | 5.3 | 5.3 | 5.3 |
| | | | | VACUUM TANK: | | | | | |
| Sizing Pressure (cm $H_2O$) | 20 | 20 | 20 | 41 | 41 | 41 | 20 | 20 | 20 |
| Water Temp (°C.) | 10 | 10 | 10 | 10 | 10 | 10 | 10 | 10 | 10 |
| | | | | PULLER: | | | | | |
| Speed (cm/min) | 396 | 396 | 396 | 360 | 360 | 360 | 366 | 366 | 366 |

| | | 62 | | | 63 | | | 64 | |
|---|---|---|---|---|---|---|---|---|---|
| LAYER: | A | B | C | A | B | C | A | B | C |
| MATERIAL: | EMAA | EVA | EMAZ | EMAA | EVA | EMAZ | EMAA | EVA | EMAZ |
| % VA | | 28/31 | | | 28/31 | | | 28/31 | |
| EXTRUDER BARREL (cm): | 1.3 | 2.5 | 1.9 | 1.3 | 2.5 | 1.9 | 1.3 | 2.5 | 1.9 |
| Zone 1 temp (°C.) | 168 | 172 | 168 | 168 | 172 | 168 | 168 | 172 | 168 |
| Zone 2 temp (°C.) | 182 | 177 | 177 | 182 | 177 | 177 | 181 | 177 | 177 |
| Zone 3 temp (°C.) | 174 | 177 | 179 | 174 | 177 | 179 | 174 | 177 | 179 |
| Zone 4 CLP temp (°C.) | 179 | 180 | 191 | 179 | 180 | 191 | 179 | 179 | 191 |
| Melt Tube temp (°C.) | 182 | 182 | 182 | 182 | 182 | 182 | 182 | 182 | 182 |
| Die Temp (°C.) | 182 | 182 | 182 | 182 | 182 | 182 | 182 | 182 | 182 |
| RPM | 8.9 | 16.0 | 7.5 | 4.5 | 15.3 | 2.8 | 4.6 | 13.6 | 4.0 |
| Melt Temp (°C.) | 166 | 181 | NA | 166 | 179 | NA | 166 | 182 | NA |
| Pressure | 0.9 | 9.2 | NA | 0.3 | 9.0 | NA | 0.4 | 9.2 | NA |

TABLE 20-continued

Extruder conditions for the three-layered tubings of
Examples 59–69
(A = outside layer; B = inner layer; C = inside layer).

| | Example No. | | | | | | | | |
|---|---|---|---|---|---|---|---|---|---|
| (MPa) | | | | | | | | | |
| Amps | 1.8 | 1.8 | 3.0 | 0.4 | 1.8 | 1.0 | 1.2 | 1.8 | 2.0 |
| Internal Air Pressure (cm $H_2O$) | 8.4 | 8.4 | 8.4 | 3.0 | 3.0 | 3.0 | 1.3 | 1.3 | 1.3 |
| VACUUM TANK: | | | | | | | | | |
| Sizing Pressure (cm $H_2O$) | 20 | 20 | 20 | | | | 20 | 20 | 20 |
| Water Temp (°C.) | 10 | 10 | 10 | 10 | 10 | 10 | | | |
| PULLER: | | | | | | | | | |
| Speed (cm/min) | 412 | 412 | 412 | 393 | 393 | 393 | 393 | 393 | 393 |

| | 65 | | | 66 | | | 67 | | |
|---|---|---|---|---|---|---|---|---|---|
| LAYER: | A | B | C | A | B | C | A | B | C |
| MATERIAL: | EMAA | EVA | EMAZ | EMAA | EVA | EMAZ | EMAA | EVA | EMAZ |
| % VA | | 28/31 | | | 28/31 | | | 28/31 | |
| EXTRUDER BARREL (cm): | 1.3 | 2.5 | 1.9 | 1.3 | 2.5 | 1.9 | 1.3 | 2.5 | 1.9 |
| Zone 1 temp (°C.) | 168 | 172 | 168 | 168 | 172 | 168 | 168 | 172 | 168 |
| Zone 2 temp (°C.) | 181 | 177 | 177 | 181 | 177 | 177 | 181 | 177 | 177 |
| Zone 3 temp (°C.) | 174 | 177 | 179 | 174 | 177 | 179 | 174 | 177 | 179 |
| Zone 4 CLP temp (°C.) | 179 | 179 | 191 | 179 | 179 | 191 | 179 | 179 | 191 |
| Melt Tube temp (°C.) | 182 | 182 | 182 | 182 | 182 | 182 | 182 | 182 | 182 |
| Die Temp (°C.) | 182 | 182 | 182 | 182 | 182 | 182 | 182 | 182 | 182 |
| RPM | 4.3 | 16.5 | 2.9 | 6.5 | 14.0 | 3.9 | 9.2 | 11.1 | 5.1 |
| Melt Temp (°C.) | 166 | 182 | NA | 166 | 182 | NA | 166 | 182 | NA |
| Pressure (MPa) | 0.3 | 9.7–10.3 | NA | 0.1 | 8.3 | NA | 0.3–0.4 | 7.6–8.3 | NA |
| Amps | 1.0 | 2.0 | 1.5 | 1.2 | 2.0 | 1.7 | 1.4 | 1.4 | 1.9 |
| Internal Air Pressure (cm $H_2O$) | 2.3 | 2.3 | 2.3 | 2.3 | 2.3 | 2.3 | 1.3 | 1.3 | 1.3 |
| VACUUM TANK: | | | | | | | | | |
| Sizing Pressure (cm $H_2O$) | 20 | 20 | 20 | 20 | 20 | 20 | 20 | 20 | 20 |
| Water Temp (°C.) | 10 | 10 | 10 | 10 | 10 | 10 | 10 | 10 | 10 |
| PULLER: | | | | | | | | | |
| Speed (cm/min) | | | | 381 | 381 | 381 | 381 | 381 | 381 |

| | Example No. | | | | | |
|---|---|---|---|---|---|---|
| | 68 | | | 69 | | |
| LAYER: | A | B | C | A | B | C |
| MATERIAL: | EMAA | EVA | EMAZ | EMAZ | EVA | EMAA |
| % VA | | 28/31 | | | 28/31 | |
| EXTRUDER BARREL (cm): | 1.3 | 2.5 | 1.9 | 1.3 | 2.5 | 1.9 |
| Zone 1 temp (°C.) | 168 | 172 | 168 | 168 | 172 | 168 |
| Zone 2 temp (°C.) | 181 | 177 | 177 | 179 | 177 | 169 |
| Zone 3 temp (°C.) | 174 | 177 | 179 | 182 | 177 | 174 |
| Zone 4 CLP temp (°C.) | 179 | 179 | 191 | | 179 | 179 |
| Melt Tube temp (°C.) | 182 | 182 | 182 | 182 | 182 | 182 |
| Die Temp (°C.) | 182 | 182 | 182 | 182 | 182 | 182 |
| RPM | 9.2 | 20.0 | 5.2 | 19.0 | 13.1 | 13.4 |
| Melt Temp (°C.) | 166 | 182 | NA | NA | 179 | 166 |
| Pressure (MPa) | 0.3–0.4 | 11.0 | NA | NA | 7.9–8.4 | 2.4 |
| Amps | 1.4 | 2.0 | 1.9 | 1.5 | 1.8 | 1.8 |
| Internal Air Pressure (cm $H_2O$) | 1.3 | 1.3 | 1.3 | 3.0 | 3.0 | 3.0 |

TABLE 20-continued

Extruder conditions for the three-layered tubings of
Examples 59–69
(A = outside layer; B = inner layer; C = inside layer).

| | Example No. | | | | | |
|---|---|---|---|---|---|---|
| | VACUUM TANK: | | | | | |
| Sizing Pressure (cm H₂O) | | | | 20 | 20 | 20 |
| Water Temp (°C.) | 10 | 10 | 10 | | | |
| | | PULLER: | | | | |
| Speed (cm/min) | 488 | 488 | 488 | 427 | 427 | 427 |

TABLE 21

Average thicknesses for the inside layer, inner layer, outside
layer, total tubing layers, and kink/rekink resistance for the
three-layered tubings of Examples 52, 55, and 59–68.

| Example Number | Outside Layer Thick (μ) | Inner Layer Thick (μ) | Inside Layer Thick (μ) | Total Layer Thick (μ) | Kink/ Rekink |
|---|---|---|---|---|---|
| 52 | 28 | 412 | 328 | 478 | 1.5/<1.2 |
| 55 | 30 | 412 | 30 | 472 | 1.9/<1.2 |
| 59 | 269 | 241 | 31 | 541 | 1.8/<1.2 |
| 60 | 178 | 462 | 31 | 671 | 2.0/<1.2 |
| 61 | 279 | 442 | 61 | 782 | 2.2/<1.2 |
| 62 | 389 | 340 | 61 | 790 | 2.0/<1.2 |
| 63 | 130 | 330 | 71 | 531 | <1.2/<1.2 |
| 64 | 211 | 361 | 30 | 602 | 1.5/<1.2 |
| 65 | 140 | 381 | 41 | 562 | |
| 66 | 201 | 361 | 30 | 592 | |
| 67 | 180 | 259 | 41 | 480 | |
| 68 | 109 | 389 | 41 | 539 | |

TABLE 22

Results of extraction studies for three layered (ABA) tubings of
Examples 7, 10, 18 and a control.

| Example | Extraction Fluid | Zinc (micrograms/ml) | Sodium (micrograms/ml) |
|---|---|---|---|
| Control | Dextrose | | 0.7 |
| 7 | Dextrose | | 19.4 |
| Control | Saline | <0.020 | |
| 10 | Saline | 9.0 | |
| 18 | Saline | <0.020 | |
| Control | Fat Emulsion | 0.090 | |
| 10 | Fat Emulsion | 12.3 | |

While in accordance with the patent statutes, description of the preferred weight fractions, processing conditions, and product usages have been provided, the scope of the invention is not to be limited thereto or thereby. Various modifications and alterations of the present invention will be apparent to those skilled in the art without departing from the scope and spirit of the present invention. The examples described in this application are illustrative of the possibilities of varying the amounts and types of polymeric materials in the multilayered tubings and films to achieve properties for specific purposes. They are not meant as limitations of the invention. Consequently, for an understanding of the scope of the present invention, reference is made to the following claims.

We claim:

1. A multilayered medical tubing having a bore and inside and outside surfaces comprising:

a) at least one inner layer of at least one chlorine-free first thermoplastic polymer having a flexibility, measured by its Young's modulus, within a range of about 2 to about 60 megaPascals; and b) at least an outside surface layer of at least one tough, chlorine-free second thermoplastic polymer having a Young's modulus not more than about fifteen times the Young's modulus of the first thermoplastic polymer, wherein said bore has a diameter of less than 12.7 mm.

2. A multilayered tubing according to claim 1 wherein the Young's modulus of the second thermoplastic polymer is about equal to or is greater than the Young's modulus of the first thermoplastic polymer.

3. A multilayered tubing according to claim 1 wherein the Young's modulus of the second thermoplastic polymer is greater than the Young's modulus of the first thermoplastic polymer.

4. A multilayered tubing according to claim 3 wherein the Young's modulus of the second thermoplastic polymer is not more than about seven times the Young's modulus of the first thermoplastic polymer.

5. A multilayered tubing according to claim 3 wherein the Young's modulus of the second thermoplastic polymer is not more than about three times the Young's modulus of the first thermoplastic polymer.

6. A multilayered tubing according to claim 1 wherein the Young's modulus of the second thermoplastic polymer is within a range of from about 15 to 300 megaPascals.

7. A multilayered tubing according to claim 1, wherein the Young's modulus of the second thermoplastic polymer is from about 20 to about 150 megaPascals.

8. A multilayered tubing according to claim 1 having a kink-rekink resistance in a range of from greater than or equal to 1.8 as measured by a kink-o-meter test.

9. A multilayered tubing according to claim 1 having a Young's modulus within a range of about 15 to about 60 megaPascals.

10. A multilayered tubing according to claim 1 having an outer tube surface abrasion resistance within an abrasive index range of 100 or greater as measured by ASTM test D 1630-83.

11. A multilayered tubing according to claim 1 having an essentially complete resiliency and essentially no wall failure throughout at least a 24 hour period of compression testing according to the Clamp Test.

12. A multilayered tubing according to claim 1 which is environmentally compatible.

13. A multilayered tubing according to claim 1 which contains essentially no medically harmful substance capable of leaching into an aqueous based or organic based fluid carried through the tubing or surrounding the tubing.

14. A multilayered tubing according to claim 13 wherein the fluid is aqueous based and contains organic components.

15. A multilayered tubing according to claim 14 wherein the aqueous based fluid is a medical fluid, a pharmaceutical fluid or a body fluid.

16. A multilayered tubing according to claim 1 wherein the thickness ratio of the inner layer to all other layers is about 1:1 to about 30:1.

17. A multilayered tubing according to claim 1 having at least three layers, those layers at least being the outside surface layer, the inner layer and an inside surface layer of at least one tough, chlorine-free third thermoplastic polymer having a Young's modulus like that of the second thermoplastic polymer.

18. A multilayered tubing according to claim 1 having only two layers wherein the inner layer forms the inside surface of the tubing.

19. A multilayered tubing according to claim 1 having at least three layers, those layers at least being the outside surface layer, the inner layer and an inside surface layer of at least one tough, chlorine-free third thermoplastic polymer having a Young's modulus up to about fifteen times that of the first thermoplastic polymer.

20. A multilayered tubing according to claim 19 having additional layers between the outside and inside surface layers, those additional layers being comprised of at least one of the first, second and third thermoplastic polymers.

21. A multilayered tubing according to claim 1 wherein the first and second thermoplastic polymers have backbones that are linear, cross-linked, branched, random, grafted, block, crystalline-amorphous domain, pseudo-cross-linked or ionomeric.

22. A multilayered tubing according to claim 1 wherein the first and second thermoplastic polymers are polymers of olefin monomer or are copolymers of olefin monomer and substituted olefin monomer.

23. A multilayer tubing according to claim 22 wherein the olefin monomer is a C2 to C4 mono-unsaturated alkene.

24. A multilayered tubing according to claim 23 wherein the substituted olefin monomer is a C4 to C14 mono-unsaturated alkene, a C8 to C14 aryl alkene, or a C2 to C6 mono-unsaturated alkene having a moiety selected from the group consisting of oxyalkanoyl, carboxy, carboxamide and alkoxycarbonyl of 1 to 6 carbons.

25. A multilayered tubing according to claim 1 wherein the first thermoplastic polymer is a copolymer of ethylene and vinylacetate, a copolymer of ethylene arid n-butylacrylate, a copolymer of ethylene and butene or a copolymer of ethylene octene; the second thermoplastic polymer is an ionomeric ethylene-methacrylic acid copolymer with zinc, an ionomeric propylene-methacrylic acid copolymer with zinc, an ionomeric ethylene-methacrylic acid copolymer with sodium, an ionomeric propylene-methacrylic acid, copolymer with sodium, a copolymer of ethylene and butene, a copolymer of ethylene and acrylic acid, a copolymer of ethylene and vinylacetate, a copolymer of ethylene and n-butylacrylate, a copolymer of ethylene and methacrylic acid or polyethylene and the third thermoplastic polymer, if present, is an ionomeric ethylene-methacrylic acid copolymer with zinc, an ionomeric propylene-methacrylic acid copolymer with zinc, an ionomeric ethylene-methacrylic acid copolymer with sodium, an ionomeric propylene-methacrylic acid copolymer with sodium, a copolymer of ethylene and butene, a copolymer of ethylene and vinylacetate, a copolymer of ethylene and n-butyl acrylate, a copolymer of ethylene and methacrylic acid or a copolymer of ethylene and acrylic acid.

26. A multilayered tubing according to claim 23 wherein the first thermoplastic polymer is a copolymer of ethylene and vinylacetate, a copolymer of ethylene and n-butylacrylate, a copolymer of ethylene and butene or a copolymer of ethylene octene; the second thermoplastic polymer is an ionomeric ethylene-methacrylic acid copolymer with zinc, an ionomeric propylene-methacrylic acid copolymer with zinc, an ionomeric ethylene-methacrylic acid copolymer with sodium, an ionomeric propylene-methacrylic acid copolymer with sodium, a copolymer of ethylene and butene, a copolymer of ethylene and acrylic acid, a copolymer of ethylene and vinylacetate, a copolymer of ethylene and n-butylacrylate, a copolymer of ethylene and methacrylic acid or polyethylene and the third thermoplastic polymer, if present, is an ionomeric ethylene-methacrylic acid copolymer with zinc, an ionomeric propylene-methacrylic acid copolymer with zinc, an ionomeric ethylene-methacrylic acid copolymer with sodium, an ionomeric propylene-methacrylic acid copolymer with sodium, a copolymer of ethylene and butene, a copolymer of ethylene and vinylacetate, a copolymer of ethylene and n-butyl acrylate, a copolymer of ethylene and methacrylic acid or a copolymer of ethylene and acrylic acid.

27. A multilayered tubing according to claim 1, wherein the tubing is prepared by the process of melted, pressurized coextrusion of the layers.

28. A multilayered tube according to claim 1 wherein the ratio of the outside diameter of the tube to the inside diameter of the tube is 1.40 or greater.

29. A multilayered tube according to claim 1 wherein the ratio of the outside diameter of the tube to the inside diameter of the tube is 1.50 or greater.

30. A multilayered tube according to claim 1 wherein the tube is provided in a medical device selected from the group consisting of intravenous fluid administration sets, arthroscopy fluid control systems, cardiovascular systems, blood gas monitoring systems, coronary artery bypass tubes, infusion pump tubes, catheters, dialysis tubes, peritoneal lavage tubes, respiratory tubes, endotracheal tubes, gastric feeding tubes, wound drainage tubes, urinary catheter tubes, and angioplasty tubes.

31. A multilayered tube according to claim 1 wherein said bore has a diameter of less than about 6.4 min.

* * * * *

UNITED STATES PATENT AND TRADEMARK OFFICE
CERTIFICATE OF CORRECTION

PATENT NO.: 5,562,127

DATED: October 8, 1996

INVENTOR(S): Dan L. Fanselow, Walton J. Hammar, John H. Ko, James C. Margl and Debra L. Wilfong It is certified that error appears in the above-identified patent and that said Letters Patent is hereby corrected as shown below:

Cover page, Under "Related U.S. Application Data""Continuation-in-part" should read -- Continuation --.

Col. 14, line 55, "Modulusus" should read -- Modulus --.

Col. 18, line 58, Equation 1: "D" should read -- X --.

Col. 18, line 60, "Young°s" should read -- Young's --.

Col. 23, line 28, "0-95" should read -- 0.95 --.

Col. 23, line 31, "Young°s" should read -- Young's --.

Cols. 29, 30, Table 2, Col. 6, "Strain" should read -- Stress --.

Cols. 31, 32, Table 5, under the title "Vacuum Tank", in the second row titled "Water Temp (°C.)", in Cols. 5, 6, 7 and 8, "27" should read -- 32 --.

UNITED STATES PATENT AND TRADEMARK OFFICE
CERTIFICATE OF CORRECTION

PATENT NO.: 5,562,127

DATED: October 8, 1996

INVENTOR(S): Dan L. Fanselow, Walton J. Hammar, John H. Ko, James C. Margl and Debra L. Wilfong It is certified that error appears in the above-identified patent and that said Letters Patent is hereby corrected as shown below:

Col. 51, line 45, "arid" should read -- and --.

Col. 51, line 51, delete the comma after "acid".

Signed and Sealed this

Eleventh Day of March, 1997

Attest:

BRUCE LEHMAN

*Attesting Officer*                *Commissioner of Patents and Trademarks*